United States Patent
Ni et al.

(10) Patent No.: US 12,296,196 B2
(45) Date of Patent: May 13, 2025

(54) RADIATION THERAPY SYSTEM AND METHOD

(71) Applicant: SHANGHAI UNITED IMAGING HEALTHCARE CO., LTD., Shanghai (CN)

(72) Inventors: Cheng Ni, Shanghai (CN); Peng Wang, Shanghai (CN); Xing'en Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 206 days.

(21) Appl. No.: 18/065,605

(22) Filed: Dec. 13, 2022

(65) Prior Publication Data

US 2023/0113808 A1 Apr. 13, 2023

Related U.S. Application Data

(63) Continuation of application No. PCT/CN2020/096599, filed on Jun. 17, 2020.

(51) Int. Cl.
*A61N 5/10* (2006.01)
*A61B 5/055* (2006.01)
*G01R 33/48* (2006.01)

(52) U.S. Cl.
CPC ............ *A61N 5/1049* (2013.01); *A61B 5/055* (2013.01); *G01R 33/4808* (2013.01); *A61N 2005/1055* (2013.01)

(58) Field of Classification Search
CPC .......... A61N 5/1049; A61N 2005/1055; A61B 5/055; G01R 33/4808
See application file for complete search history.

(56) References Cited

U.S. PATENT DOCUMENTS

| 9,421,398 | B2 | 8/2016 | Shvartsman et al. |
| 10,960,229 | B2 * | 3/2021 | Ni .................... G01R 33/3403 |
| 11,986,674 | B2 * | 5/2024 | Ni ........................ A61N 5/1081 |

(Continued)

FOREIGN PATENT DOCUMENTS

| KR | 20150049317 A | 5/2015 |
| WO | 2011127946 A1 | 10/2011 |
| WO | 2015197475 A1 | 12/2015 |

OTHER PUBLICATIONS

International Search Report in PCT/CN2020/096599 mailed on Mar. 19, 2021, 6 pages.

(Continued)

*Primary Examiner* — Baisakhi Roy
(74) *Attorney, Agent, or Firm* — METIS IP LLC

(57) ABSTRACT

The present disclosure is directed to a radiation therapy system. The radiation therapy system may comprise a magnetic resonance imaging (MRI) apparatus configured to acquire MRI data with respect to a region of interest (ROI) of a subject, the MRI apparatus including a magnetic body; and a radiation therapy apparatus configured to apply a radiation beam to at least one portion of the ROI. The radiation therapy apparatus may include a linear accelerator configured to accelerate electrons to produce the radiation beam, the linear accelerator being located in a bore formed by an inner surface of the magnetic body, and a length direction of the linear accelerator being parallel with an axis of the magnetic body.

20 Claims, 16 Drawing Sheets

(56) References Cited

U.S. PATENT DOCUMENTS

| | | |
|---|---|---|
| 2001/0001807 A1 | 5/2001 | Green |
| 2008/0208036 A1 | 8/2008 | Amies et al. |
| 2011/0012593 A1* | 1/2011 | Shvartsman ....... G01R 33/3806 |
| | | 324/307 |
| 2011/0196227 A1 | 8/2011 | Gross et al. |
| 2011/0213239 A1* | 9/2011 | Amies .................. A61N 5/1049 |
| | | 600/411 |
| 2011/0218420 A1* | 9/2011 | Carlone ............. G01R 33/4812 |
| | | 600/411 |
| 2011/0260729 A1 | 10/2011 | Carlone et al. |
| 2013/0225975 A1 | 8/2013 | Harvey |
| 2014/0135615 A1* | 5/2014 | Kruip ................... A61N 5/1081 |
| | | 600/411 |
| 2014/0266208 A1* | 9/2014 | Dempsey ........... G01R 33/3607 |
| | | 29/601 |
| 2015/0251020 A1 | 9/2015 | Calone et al. |
| 2017/0361128 A1 | 12/2017 | Lachaine et al. |
| 2020/0147412 A1 | 5/2020 | Ni et al. |
| 2020/0246637 A1* | 8/2020 | Wang ..................... A61B 5/055 |
| 2020/0408866 A1* | 12/2020 | Vesanen ............. G01R 33/4838 |
| 2021/0393983 A1* | 12/2021 | Ni ........................ A61N 5/1039 |
| 2023/0017149 A1* | 1/2023 | Shvartsman ....... G01R 33/4808 |
| 2023/0113808 A1* | 4/2023 | Ni ........................ A61N 5/1049 |
| | | 600/410 |

OTHER PUBLICATIONS

Written Opinion in PCT/CN2020/096599 mailed on Mar. 19, 2021, 5 pages.
First Office Action in Chinese Application No. 202080101205.2 mailed on Apr. 18, 2024, 17 pages.

* cited by examiner

RADIATION THERAPY SYSTEM AND METHOD

CROSS-REFERENCE TO RELATED APPLICATIONS

This application is a continuation of International Application No. PCT/CN2020/096599, filed on Jun. 17, 2020, the contents of which are hereby incorporated by reference.

TECHNICAL FIELD

The present disclosure generally relates to a radiation therapy system, and more particularly, relates to an image-guided radiation therapy system that combines radiation therapy and magnetic resonance imaging techniques.

BACKGROUND

Radiation therapy on a subject (e.g., a tumor) is currently affected by difficulties to track the variation (e.g., motion) of the subject in different treatment sessions. Nowadays, various imaging techniques may be applied to provide real-time images of the subject before or within each treatment session. For example, a magnetic resonance imaging (MRI) apparatus may be used in combination with a radiation therapy apparatus to provide MR images of the subject. The combination of the MRI apparatus and the radiation therapy apparatus, which forms an MRI image-guided therapeutic apparatus, may encounter difficulties in arranging components of the MRI apparatus (e.g., a plurality of main magnetic coils, a plurality of shielding magnetic coils, one or more gradient coils, etc.) and components of the radiation therapy apparatus (e.g., a linear accelerator) in a relatively compact space without causing interferences. Therefore, it may be desirable to provide a therapeutic apparatus that provides high therapeutic quality and also has a compact structure as well.

SUMMARY

According to an aspect of the present disclosure, a radiation therapy system is provided. The radiation therapy system may comprise a magnetic resonance imaging (MRI) apparatus configured to acquire MRI data with respect to a region of interest (ROI) of a subject, the MRI apparatus including a magnetic body; and a radiation therapy apparatus configured to apply a radiation beam to at least one portion of the ROI. The radiation therapy apparatus may include a linear accelerator configured to accelerate electrons to produce the radiation beam, the linear accelerator being located in a bore formed by an inner surface of the magnetic body, and a length direction of the linear accelerator being parallel with an axis of the magnetic body.

In some embodiments, the MRI apparatus further includes one or more gradient coils arranged in the bore, the one or more gradient coils being around the axis of the magnetic body.

In some embodiments, the one or more gradient coils are split gradient coils.

In some embodiments, the linear accelerator is arranged within an opening formed by inner surfaces of the one or more gradient coils.

In some embodiments, the linear accelerator is disposed at or close to an end of the bore.

In some embodiments, the radiation therapy apparatus further includes an annular radiation shielding component surrounding the linear accelerator.

In some embodiments, the linear accelerator is located in a gap between two neighboring split gradient coils.

In some embodiments, the linear accelerator is arranged at or close to a mid-point of the bore in a length direction of the bore.

In some embodiments, the radiation therapy apparatus further includes a radiation shielding component surrounding a portion of the linear accelerator, the surrounded portion of the linear accelerator being closer to the axis of the magnetic body.

In some embodiments, the radiation therapy apparatus further includes at least one deflection magnet configured to deflect the electrons towards a target, the radiation beam being produced when the electrons collide onto the target.

In some embodiments, a distance between the target and the axis of the magnetic body is greater than a distance between the linear accelerator and the axis of the magnetic body.

In some embodiments, the linear accelerator is located away from a path of the radiation beam from the target to the at least one portion of the ROI.

In some embodiments, the linear accelerator is located at a first position corresponding to a first circumferential angle of the bore, the target is located at a second position corresponding to a second circumferential angle of the bore, and the first circumferential angle is unequal to the second circumferential angle.

In some embodiments, the at least one deflection magnet includes a permanent magnet.

In some embodiments, the radiation therapy apparatus includes a microwave device configured to accelerate the electrons, the microwave device being operably coupled to the linear accelerator through a waveguide.

In some embodiments, the magnetic body includes a plurality of main magnetic coils; a plurality of shielding coils, the plurality of shielding magnetic coils being around the axis of the magnetic body, and located along a circumference, or a portion thereof, with a larger radius from the axis of the magnetic body than the plurality of main magnetic coils; and an annular cryostat in which the plurality of main magnetic coils and the plurality of shielding coils are arranged.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Figure 3:
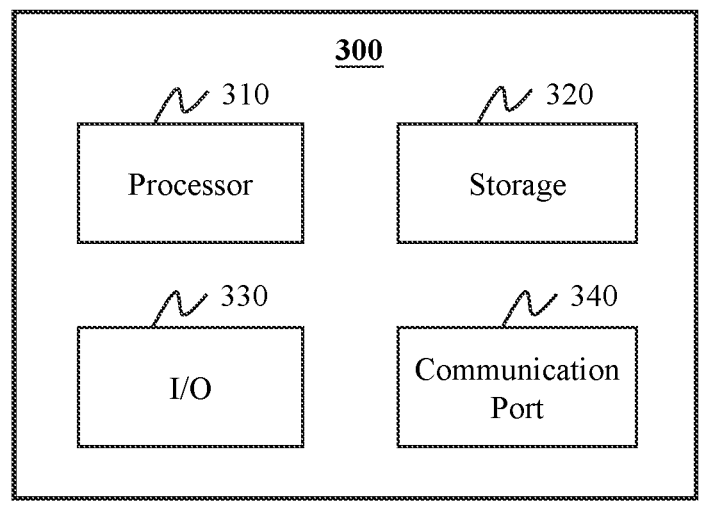
FIG. 3 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are apparatus for medical application, such as for disease treatment and/or diagnostic purposes. While the apparatus disclosed in the present disclosure are described primarily regarding a magnetic resonance imaging-radiotherapy (MRI-RT) system. It should be understood that this is only for illustration purposes. In some embodiments, the imaging system may include a positron emission tomograhy-radiotherapy (PET-RT) system, an emission computed tomography-radiothreraphy (ECT-RT) system, a computed tomography-radiothreraphy (CT-RT) system, etc.

An aspect of the present disclosure relates to a radiation therapy system. The radiation therapy system may include an MRI apparatus and a radiation therapy apparatus. The MRI apparatus may include a magnetic body. The radiation therapy apparatus may include a linear accelerator configured to accelerate electrons to produce the radiation beam. The linear accelerator may be located in a bore formed by an inner surface of the magnetic body instead of being located out of the bore in conventional MRI-RT systems. In this case, a source-to-axis distance (SAD) from a radiation source of the radiation therapy apparatus to a rotation axis of the gantry may be smaller than that of conventional MRI-RT systems. In addition, a length direction of the linear accelerator may be parallel with an axis of the magnetic body. The length direction of the linear accelerator may be parallel with the direction of main magnetic field generated by the magnetic body. Thus, the effect of the main magnetic field on the acceleration of electrons in the linear accelerator may be removed or reduced, and magnetic shielding for the linear accelerator may be omitted.

Figure 1:
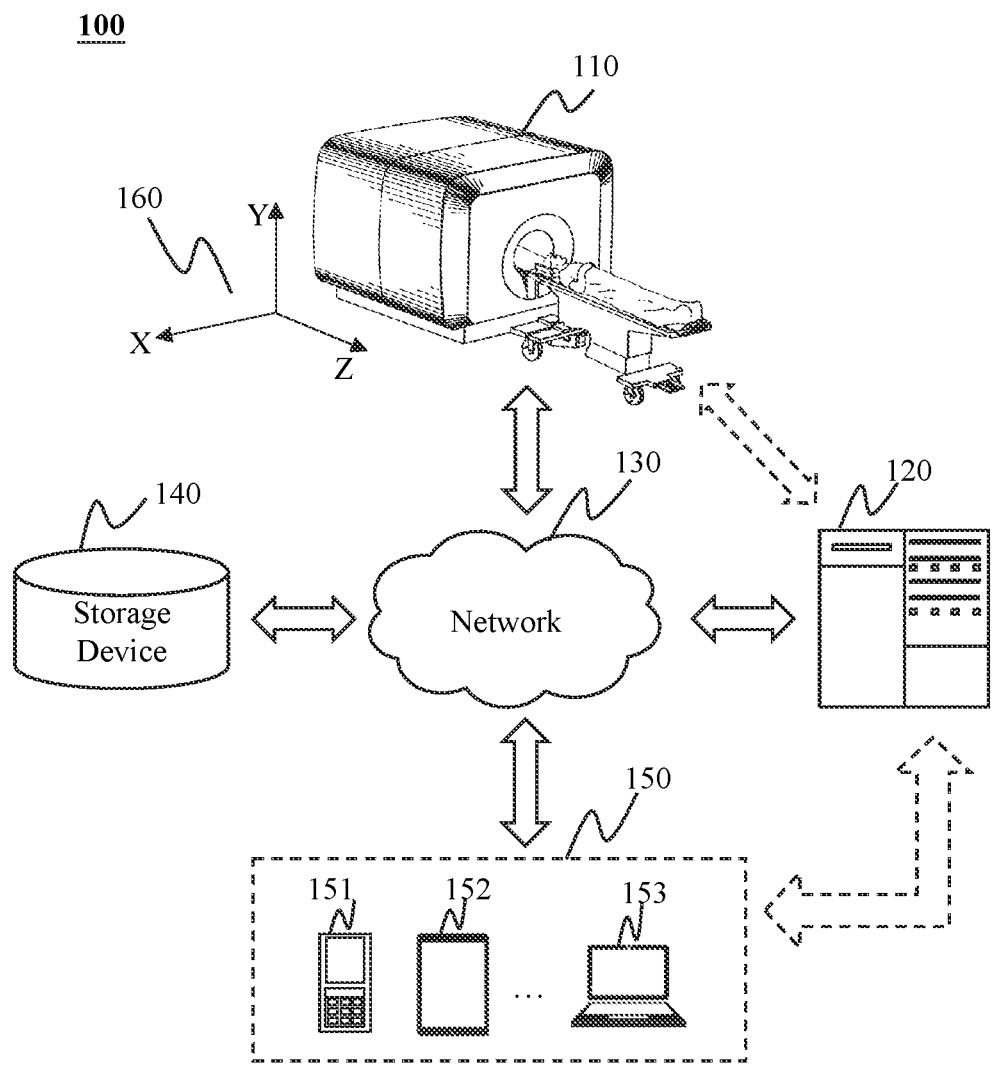
FIG. 1 is a block diagram illustrating an exemplary radiation therapy system according to some embodiments of the present disclosure.

FIG. 1 is a block diagram illustrating an exemplary radiation therapy system 100 according to some embodiments of the present disclosure. In some embodiments, the radiation therapy system 100 may be a multi-modality imaging system including, for example, a magnetic resonance imaging-radiotherapy (MRI-RT) system, a positron emission tomograhy-radiotherapy (PET-RT) system, etc. For better understanding the present disclosure, an MRI-RT system may be described as an example of the radiation therapy system 100, and not intended to limit the scope of the present disclosure.

As shown in FIG. 1, the radiation therapy system 100 may include a therapeutic apparatus 110, one or more processing devices 120, a network 130, a storage device 140, and one or more terminal devices 150. In some embodiments, the therapeutic apparatus 110, the one or more processing devices 120, the storage device 140, and/or the terminal device 150 may be connected to and/or communicate with each other via a wireless connection (e.g., the wireless connection provided by the network 130), a wired connection (e.g., the wired connection provided by the network 130), or any combination thereof.

The therapeutic apparatus 110 may include an MRI apparatus. The MRI apparatus may generate image data associated with MR signals generated by scanning a subject or a portion thereof. In some embodiments, the subject may include a body, a substance, an object, or the like, or any combination thereof. In some embodiments, the subject may include a specific portion of a body, a specific organ, or specific tissue, etc. For example, the subject may include the head, the brain, the neck, the body, shoulders, arms, the thorax, the heart, the stomach, blood vessels, soft tissue, knees, feet, etc., of a patient. The MRI apparatus may include a permanent magnet MRI scanner, a superconducting electromagnet MRI scanner, or a resistive electromagnet MRI scanner, etc., according to a type of a magnetic body of the MRI apparatus. In some embodiments, the MRI apparatus may include a high-field MRI scanner, a mid-field MRI scanner, and a low-field MRI scanner, etc., according to an intensity of the magnetic field generated by the MRI apparatus. In some embodiments, the MRI apparatus may be of a closed-bore (cylindrical) type, an open-bore type, or the like. In some embodiments, the therapeutic apparatus 110 may transmit, via the network 130, the image data to the one or more processing devices 120, the storage device 140, and/or the terminal device 150 for further processing. For example, the image data may be sent to the one or more processing devices 120 for generating an MR image, or may be stored in the storage device 140.

For illustration purposes, a coordinate system 160 including an X axis, a Y axis, and a Z axis (also referred to as X direction, Y direction, and Z direction, respectively) is provided in FIG. 1. The X axis and the Z axis shown in FIG. 1 may be horizontal, and the Y axis may be vertical. As illustrated, the positive X direction along the X axis may be from the right side to the left side of the therapeutic apparatus 110 seen from the direction facing the front side of the therapeutic apparatus 110; the positive Y direction along the Y axis shown in FIG. 1 may be from the lower part to the upper part of the therapeutic apparatus 110; the positive Z direction along the Z axis shown in FIG. 1 may refer to a direction from the back side to the front side of the therapeutic apparatus 110, in which the subject is moved out of an imaging or treatment channel (or referred to as an imaging or treatment bore) of the therapeutic apparatus 110.

In some embodiments, the MRI apparatus of the therapeutic apparatus 110 may be directed to select an anatomical slice of the subject along a slice selection direction and scan the anatomical slice to acquire a plurality of echo signals from the slice. During the scan, spatial encoding within the slice may be implemented by spatial encoding coils (e.g., an X coil and a Y coil) along a phase encoding direction and a frequency encoding direction. The echo signals may be sampled and the corresponding sampled data may be stored into a K-space matrix for generating image data of the subject or a portion thereof. For illustration purposes, the slice-selection direction herein may correspond to the Z direction defined by the coordinate system 160 and a Kz direction in K-space; the phase-encoding direction may correspond to the Y direction defined by the coordinate system 160 and a Ky direction in K-space; and the frequency-encoding direction may correspond to the X direction defined by the coordinate system 160 and a Kx direction in K-space. It should be noted that the slice-selection direction, the phase-encoding direction, and the frequency-encoding direction may be modified according to actual needs, and the modification may do not depart the scope of the present disclosure. More description of the MRI apparatus may be found elsewhere in the present disclosure. See, e.g., FIG. 2A and the description thereof.

The therapeutic apparatus 110 may also include a radiation therapy apparatus. The radiation therapy apparatus may apply a radiation beam to a target region of the subject. The radiation beam may include a particle ray beam, a photon ray beam, etc. Exemplary particle rays may include neutron, proton, electron, μ-meson, heavy ion, α-ray, or the like, or any combination thereof. Exemplary photon rays may include X-ray, γ-ray, ultraviolet, laser, or the like, or any combination thereof. For illustration purposes, a radiation therapy apparatus providing an X-ray beam may be described as an example.

In some embodiments, the radiation therapy apparatus may be operably coupled to the MRI apparatus. In some embodiments, one or more components of the radiation therapy apparatus may be arranged in the MRI apparatus. For example, a linear accelerator of the radiation therapy apparatus may be arranged in a scanning channel for placing the subject (also referred to as a bore) of the MRI apparatus. As another example, at least one deflection magnet of the radiation therapy apparatus may also be arranged in the bore of the MRI apparatus.

In some embodiments, the MRI apparatus may acquire image data of the subject before, during, and/or after at least a portion of a radiation therapy is performed on the subject. The radiation therapy apparatus may apply the radiation beam to the target region of the subject based at least in part on the image data provided by the MRI apparatus. Since radiation therapy on target region may be affected by difficulties to track the variation (e.g., motion) of the target region in different treatment sessions. The image data provided by the MRI apparatus may be applied to provide substantially real-time images of the target region before or within the treatment sessions. For example, the image data may be reconstructed to generate an image of the subject so as to locate the target region of the subject and/or determine the dose of the X-ray beam. As another example, the MRI image data, without being reconstructed to an MRI image, may be used to identify a motion of the subject, which may be used to guide the delivery of the radiation beam to the target region of the subject.

The subject may be placed on a treatment table. The treatment table may support the subject for imaging using the MRI apparatus and/or radiation treatment using the radiation therapy apparatus. The treatment table may be moveable back and forth along a longitudinal direction (i.e., the Z direction in FIG. 1) of the treatment table. The longitudinal direction of the treatment table may be parallel to an axial direction of the bore of the MRI apparatus. If the subject needs to be treated, the treatment table carrying the subject may be moved to a treatment position. If the subject needs to be imaged, the treatment table carrying the subject may be moved to an imaging position.

The one or more processing devices 120 may process data and/or information obtained from the therapeutic apparatus 110, the storage device 140, and/or the terminal device 150. For example, the one or more processing devices 120 may process image data, and reconstruct at least one MR image based on the image data. As another example, the one or more processing devices 120 may determine a position of a treatment region and a dose of radiation to be delivered to the treatment region based on the at least one MR image. The MR image may have advantages such as a superior soft-tissue contrast, a high resolution, and geometric accuracy, which may allow accurate positioning of the treatment region. The MR image may be used to detect a variance of the treatment region (e.g., a variance of the thorax due to the breath of the subject) during the radiation therapy, such that a treatment plan of the radiation therapy may be adjusted accordingly.

In the treatment plan, the dose of radiation may be determined according to, for example, synthetic electron density information. In some embodiments, the synthetic electron density information may be generated based on the MR image.

In some embodiments, the one or more processing devices 120 may be a single processing engine that communicates with and process data from the MRI apparatus and the radiation therapy apparatus of the therapeutic apparatus 110. In some embodiments, the one or more processing devices 120 may include at least two processing devices. One of the at least two processing devices may communicate with and process data from the MRI apparatus of the therapeutic apparatus 110, and another one of the at least two processing devices may communicate with and process data from the radiation therapy apparatus of the therapeutic apparatus 110. The at least two processing devices may communicate with each other.

In some embodiments, the one or more processing devices 120 may be a single server or a server group. The server group may be centralized or distributed. In some embodiments, the one or more processing devices 120 may be local to or remote from the therapeutic apparatus 110. For example, the one or more processing devices 120 may access information and/or data from the therapeutic apparatus 110, the storage device 140, and/or the terminal device 150 via the network 130. As another example, the one or more processing devices 120 may be directly connected to the therapeutic apparatus 110, the terminal device 150, and/or the storage device 140 to access information and/or data. In some embodiments, the one or more processing devices 120 may be implemented on a cloud platform. The cloud platform may include a private cloud, a public cloud, a hybrid cloud, a community cloud, a distributed cloud, an inter-cloud, a multi-cloud, or the like, or any combination thereof.

The network 130 may include any suitable network that can facilitate the exchange of information and/or data for the radiation therapy system 100. In some embodiments, one or more components of the radiation therapy system 100 (e.g., the therapeutic apparatus 110, the one or more processing devices 120, the storage device 140, or the terminal device 150) may communicate information and/or data with one or more other components of the radiation therapy system 100 via the network 130. For example, the one or more processing devices 120 may obtain image data from the therapeutic apparatus 110 via the network 130. As another example, the one or more processing devices 120 may obtain user instructions from the terminal device 150 via the network 130. The network 130 may include a public network (e.g., the Internet), a private network (e.g., a local area network (LAN), a wide area network (WAN)), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, or the like, or any combination thereof. In some embodiments, the network 130 may include one or more network access points. For example, the network 130 may include wired and/or wireless network access points such as base stations and/or internet exchange points through which one or more components of the radiation therapy system 100 may be connected to the network 130 to exchange data and/or information.

The storage device 140 may store data, instructions, and/or any other information. In some embodiments, the storage device 140 may store data obtained from the one or more processing devices 120 and/or the terminal device 150. In some embodiments, the storage device 140 may store data and/or instructions that the one or more processing devices 120 may execute or use to perform exemplary methods described in the present disclosure. In some embodiments, the storage device 140 may include a mass storage device, a removable storage device, a cloud based storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 140 may be implemented on a cloud platform as described elsewhere in the present disclosure.

In some embodiments, the storage device 140 may be connected to the network 130 to communicate with one or more other components of the radiation therapy system 100 (e.g., the one or more processing devices 120 or the terminal device 150). One or more components of the radiation therapy system 100 may access the data or instructions stored in the storage device 140 via the network 130. In some embodiments, the storage device 140 may be part of the one or more processing devices 120.

The terminal device 150 may be connected to and/or communicate with the therapeutic apparatus 110, the one or more processing devices 120, and/or the storage device 140. For example, the one or more processing devices 120 may acquire a treatment plan from the terminal device 150. As another example, the terminal device 150 may obtain image data from the therapeutic apparatus 110 and/or the storage device 140. In some embodiments, the terminal device 150 may include a mobile device 151, a tablet computer 152, a laptop computer 153, or the like, or any combination thereof. For example, the mobile device 151 may include a mobile phone, a personal digital assistance (PDA), a laptop, a tablet computer, a desktop, or the like, or any combination thereof. In some embodiments, the terminal device 150 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the one or more processing devices 120 via, for example, a bus, for further processing. Other types of the input device may include a cursor control device, such as a mouse, a trackball, or cursor direction keys, etc. The output device may include a display, a speaker, a printer, or the like, or any combination thereof. In some embodiments, the terminal device 150 may be part of the one or more processing devices 120.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the storage device 140 may be a data storage including cloud computing platforms, such as public cloud, private cloud, community, hybrid clouds, etc. In some embodiments, the one or more processing devices 120 may be integrated into the therapeutic apparatus 110. As another example, the radiation therapy system 100 may further include a control device configured to determine one or more parameters of the therapeutic apparatus 110 so as to optimize the imaging and/or radiation treatment of the subject. In some embodiments, the control device may be part of the processing device 120 and/or the terminal 150. However, those variations and modifications do not depart the scope of the present disclosure.

Figure 2A:
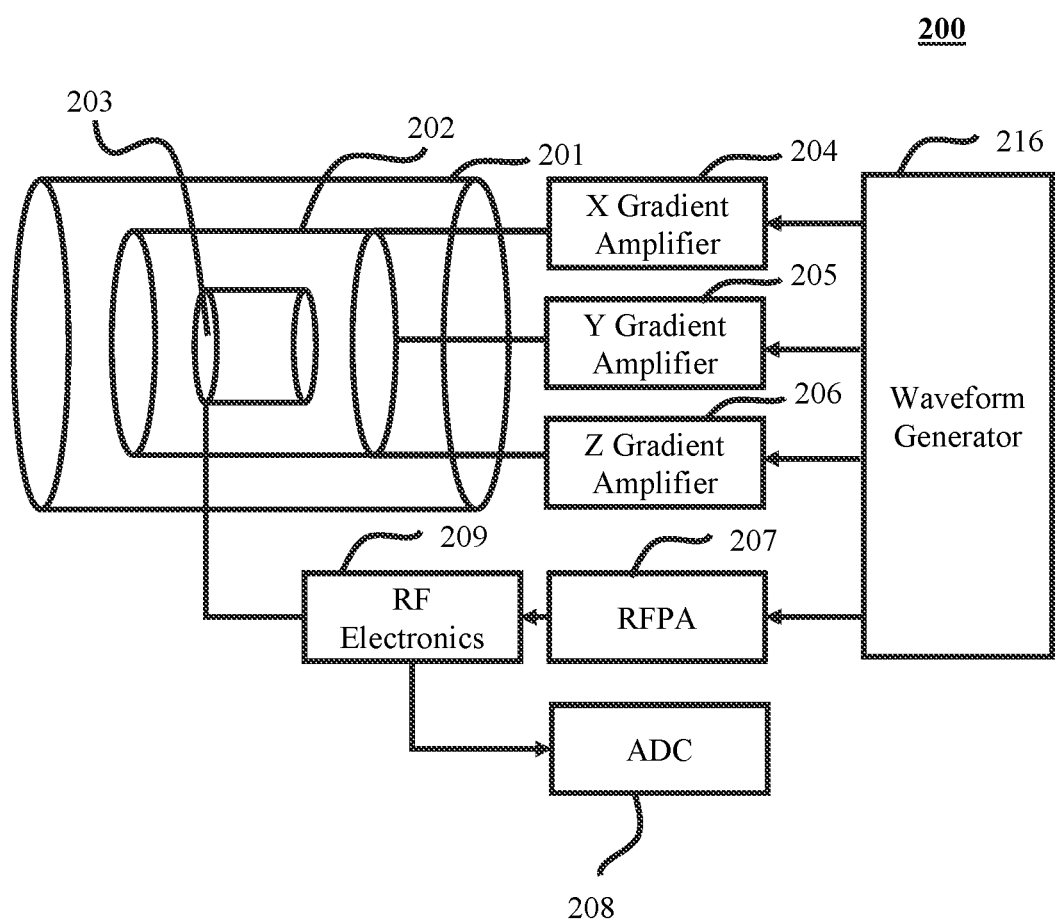
FIG. 2A is a schematic diagram illustrating exemplary components of an MRI apparatus according to some embodiments of the present disclosure.

FIG. 2A is a schematic diagram illustrating exemplary components of an MRI apparatus according to some embodiments of the present disclosure. One or more components of the MRI apparatus 200 are illustrated in FIG. 2A. As illustrated, a main magnet 201 may generate a first magnetic field (or referred to as a main magnetic field) that may be applied to a subject (also referred to as an object) exposed inside the field. The main magnet 201 may include a resistive magnet or a superconductive magnet that both need a power supply (not shown) for operation. Alternatively, the main magnet 201 may include a permanent magnet. The main magnet 201 may include a bore within which the subject is placed. The main magnet 201 may also control the homogeneity of the generated main magnetic field. One or more shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of a subject may vary as a function of their positions inside the gradient field, thereby encoding spatial information into echo signals generated by the region of the subject being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2A). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of echo signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MR scanner or an open-bore MR scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2A are the same as or similar to those described in FIG. 1.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate echo signals related to the region of the subject being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting echo signals. After excitation, the echo signals generated by the subject may be sensed by the RF coils 203. The receive amplifier then may receive the sensed echo signals from the RF coils 203, amplify the sensed echo signals, and provide the amplified echo signals to the ADC 208. The ADC 208 may transform the echo signals from analog signals to digital signals. The digital echo signals then may be sent to the processing device 120 for sampling.

In some embodiments, the gradient coils 202 and the RF coils 203 may be circumferentially positioned with respect to the subject. It is understood by those skilled in the art that the main magnet 201, the gradient coils 202, and the RF coils 203 may be situated in a variety of configurations around the subject.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI apparatus 200 may further include a subject positioning system (not shown). The subject positioning system may include a subject cradle and a transport device. The subject may be placed on the subject cradle and be positioned by the transport device within the bore of the main magnet 201.

An MRI apparatus (e.g., the MRI apparatus 200 disclosed in the present disclosure) may be commonly used to obtain an interior image from a patient for a particular region of interest (ROI) that can be used for the purposes of, e.g., diagnosis, treatment, or the like, or a combination thereof. The MRI apparatus may include a main magnet (e.g., the main magnet 201) assembly for providing a strong uniform main magnetic field to align the individual magnetic moments of the H atoms within the patient's body. During this process, the H atoms oscillate around their magnetic poles at their characteristic Larmor frequency. If the tissue is subjected to an additional magnetic field, which is tuned to the Larmor frequency, the H atoms absorb additional energy, which rotates the net aligned moment of the H atoms. The additional magnetic field may be provided by an RF excitation signal (e.g., the RF signal generated by the RF coils 203). When the additional magnetic field is removed, the magnetic moments of the H atoms rotate back into alignment with the main magnetic field thereby emitting an echo signal. The echo signal is received and processed to form an MR image. T1 relaxation may be the process by which the net magnetization grows/returns to its initial maximum value parallel to the main magnetic field. T1 may be the time constant for regrowth of longitudinal magnetization (e.g., along the main magnetic field). T2 relaxation may be the process by which the transverse components of magnetization decay or dephase. T2 may be the time constant for decay/dephasing of transverse magnetization.

If the main magnetic field is uniform across the entire body of the patient, then the RF excitation signal may excite all of the H atoms in the sample non-selectively. Accordingly, in order to image a particular portion of the patient's body, magnetic field gradients Gx, Gy, and Gz (e.g., generated by the gradient coils 202) in the x, y, and z directions, having a particular timing, frequency, and phase, may be superimposed on the uniform magnetic field such that the RF excitation signal excites the H atoms in a desired slice of the patient's body, and unique phase and frequency information is encoded in the echo signal depending on the location of the H atoms in the "image slice."

Typically, portions of the patient's body to be imaged are scanned by a sequence of measurement cycles in which the RF excitation signals and the magnetic field gradients Gx, Gy and Gz vary according to an MRI imaging protocol that is being used. A protocol may be designed for one or more tissues to be imaged, diseases, and/or clinical scenarios. A protocol may include a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include a fast spin echo (FSE) pulse sequence, a turbo spin echo (TSE) pulse sequence, a rapid acquisition with relaxation enhancement (RARE) pulse sequence, a half-Fourier acquisition single-shot turbo spin-echo (HASTE) pulse sequence, a turbo gradient spin echo (TGSE) pulse sequence, or the like, or any combination thereof. As another example, the gradient echo sequences may include a balanced steady-state free precession (bSSFP) pulse sequence, a spoiled gradient echo (GRE) pulse sequence, and an echo planar imaging (EPI) pulse sequence, a steady state free precession (SSFP), or the like, or any combination thereof. The protocol may also include information regarding image contrast and/or ratio, an ROI, slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof. For each MRI scan, the resulting echo signals may be digitized and processed to reconstruct an image in accordance with the MRI imaging protocol that is used.

Figure 2B:
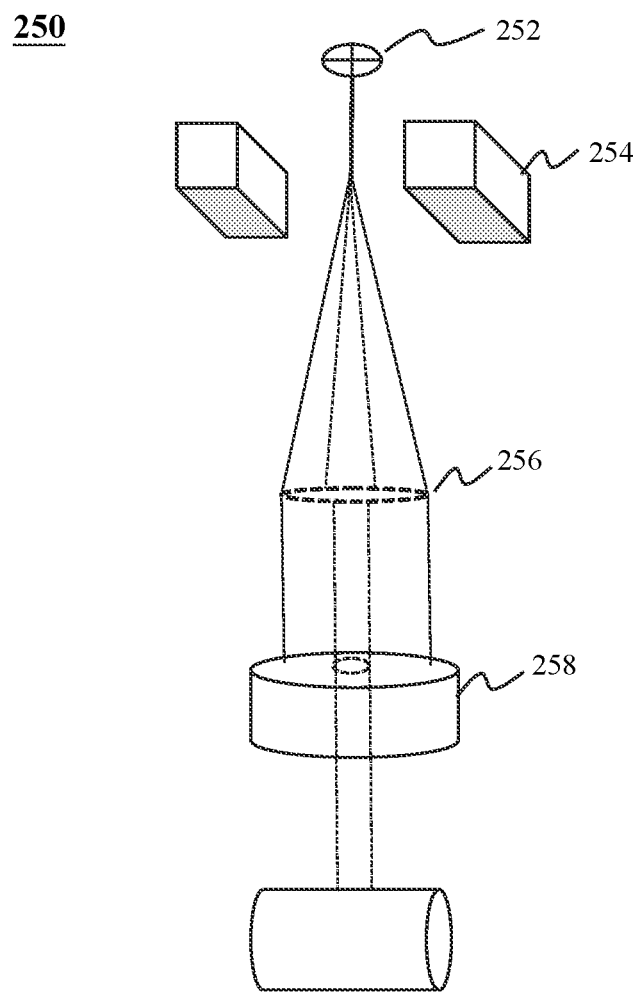
FIG. 2B is a schematic diagram illustrating exemplary components of a radiation therapy apparatus according to some embodiments of the present disclosure.

FIG. 2B is a schematic diagram illustrating exemplary components of a radiation therapy apparatus according to some embodiments of the present disclosure. As illustrated in FIG. 2B, the radiation therapy apparatus 250 may include a radiation beam generator 252, a beam control device 254, a target 256, and a treatment head 258. The radiation beam generator 252 may be configured to generate a radiation particle beam. For example, the radiation particle beam may include neutrons, electrons, hadrons (e.g., protons, ions), or other types of radiation particles. The descriptions in the following figures are provided with reference to a radiation particle beam of electrons. It can be understood that it is for illustration purposes and not intended to be limiting.

In some embodiments, the radiation beam generator 252 may include a linear accelerator (also referred to as "Linac"). The linear accelerator may be configured to accelerate electrons in an accelerating tube of the linear accelerator to form an electron beam with a certain energy level. For example, the electrons may be accelerated to form an electron beam with a high energy level in the accelerating tube. An electron beam with a high energy level refers to an electron beam with an energy greater than a threshold energy. The threshold energy may be, for example, 5 Mev, 10 Mev, 20 Mev, 30 MeV, 40 MeV, 50 MeV, 100 MeV, 200 MeV, etc. Correspondingly, an electron beam with an energy lower than the threshold energy may be referred to as an electron beam with a low energy level.

The beam control device 254 may be configured to control the radiation particle beam generated by the radiation beam generator 252. For example, the radiation particle beam generated by the radiation beam generator 252 may be deflected, defocused, and/or focused by the beam control device 254. In some embodiments, the beam control device 254 may control the radiation particle beam to achieve a desired position, direction, spatial distribution, energy distribution, beam shape, etc. As used herein, a position may refer to a point or an area on a target (e.g., a tungsten plate, a molybdenum plate, etc.) onto which the electrons in the radiation particle beam collide. A direction may refer to a direction towards which the electrons in radiation particle beam emits. A spatial distribution may refer to a distribution of the electrons in the radiation particle beam in a three-dimensional space. An energy distribution may refer to a distribution of the energy of the electrons in the radiation particle beam. A beam shape may refer to a shape of a cross-section of the radiation particle beam.

In some embodiments, the beam control device 254 may include a deflection device and a beam profile modulator. The deflection device may be configured to deflect the radiation particle beam. Merely by way of example, the radiation beam generator 252 may emit an electron beam toward a direction, which may pass through the deflection device before reaching the subject. The trajectory (e.g., the position and the direction) of the electron beam may be altered by the deflection device when it passes through the deflection device. Exemplary deflection devices may include a microwave cavity, a magnet (e.g., a permanent magnet, an electromagnet, etc.), a magnetic lens, or the like, or any combination thereof. The beam profile modulator may be configured to control the beam shape of the radiation particle beam. Merely by way of example, the beam profile modulator may include one or more beam-limiting devices, such as a blocker, that may block a specific portion of the radiation particle beam.

The target 256 may produce radiation beam for radiation treatment of the subject (e.g., the target region of the subject) when the accelerated electron beam collides on the target 256. For example, the electron beam emitted from the radiation beam generator 252 may be deflected onto the target 256 to generate X-rays at a high energy level according to the bremsstrahlung effect. In some embodiments, the target 256 may be made of a material including aluminum, copper, silver, tungsten, or the like, or an alloy thereof, or any combination thereof.

The treatment head 258 may be located at a specific location and treat the subject using the radiation beam from a specific angle. In some embodiments, one or more components of the beam control device 254 may be mounted on or integrated into the treatment head 258. For example, a beam profile modulator, such as a collimator, may be integrated into the treatment head 258. During a radiation treatment, a gantry supporting one or more components of the radiation therapy apparatus may be rotatable along an axis, and the treatment head 258 and the beam control device 254 may rotate with the gantry. For example, the gantry may rotate around the Z axis on the X-Y plane defined according to the coordinate system 160 as shown in FIG. 1.

In some embodiments, the radiation therapy apparatus may include a plurality of treatment heads, each of which may be equipped with a beam control device 254. A beam control device 254 (e.g., a multi-leaf collimator (MLC)) may be mounted on or integrated into the corresponding treatment head. In some embodiments, the radiation beam generator 252 and the beam control device 254 may be an integral assembly.

FIG. 3 is a schematic diagram illustrating exemplary hardware and/or software components of a computing device 300 according to some embodiments of the present disclosure. The computing device 300 may be used to implement any component of the radiation therapy system 100 as described herein. For example, the processing device 120 and/or the terminal 150 may be implemented on the computing device 300, respectively, via its hardware, software program, firmware, or a combination thereof. Although only one such computing device is shown, for convenience, the computer functions relating to the radiation therapy system 100 as described herein may be implemented in a distributed fashion on a number of similar platforms, to distribute the processing load. As illustrated in FIG. 3, the computing device 300 may include a processor 310, a storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process data obtained from the MRI apparatus 200, the terminal(s) 150, the storage device 140, and/or any other component of the radiation therapy system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors, thus operations and/or method operations that are performed by one processor as described in the present disclosure may also be jointly or separately performed by the multiple processors. For example, if in the present disclosure the processor of the computing device 300 executes both operation A and operation B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the MRI apparatus 200, the storage device 140, the terminal(s) 150, and/or any other component of the radiation therapy system 100. In some embodiments, the storage 320 may include a mass storage device, a removable storage device, a volatile read-and-write memory, a read-only memory (ROM), or the like, or any combination thereof. In some embodiments, the storage 320 may store one or more programs and/or instructions to perform exemplary methods described in the present disclosure. For example, the storage 320 may store a program for the processing device 120 to execute for generating an image of a region of interest (ROI) of the subject.

The I/O 330 may input and/or output signals, data, information, etc. In some embodiments, the I/O 330 may enable a user interaction with the processing device 120. In some embodiments, the I/O 330 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 340 may be connected to a network (e.g., the network 130) to facilitate data communications. The communication port 340 may establish connections between the processing device 120 and the MRI apparatus 200, the terminal(s) 150, and/or the storage device 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
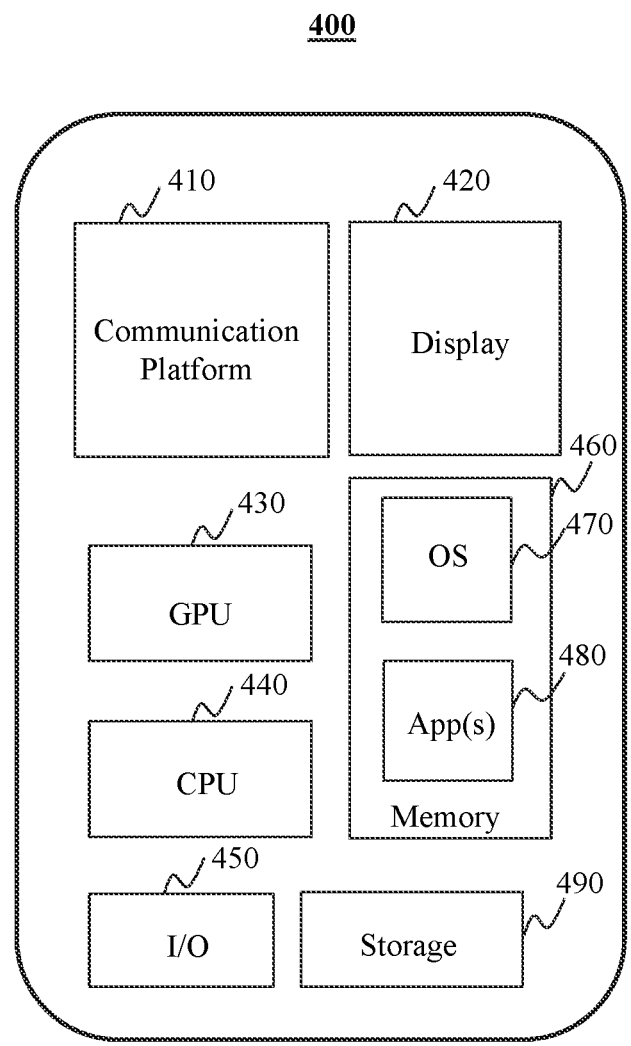
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device 400 according to some embodiments of the present disclosure. In some embodiments, one or more components (e.g., a terminal 150 and/or the processing device 120) of the radiation therapy system 100 may be implemented on the mobile device 400.

As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™) and one or more applications 480 may be loaded into the memory 460 from the storage 490 in order to be executed by the CPU 440. The applications 480 may include a browser or any other suitable mobile apps for receiving and rendering information relating to the radiation therapy system 100. User interactions with the information stream may be achieved via the I/O 450 and provided to the processing device 120 and/or other components of the radiation therapy system 100 via the network 130.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
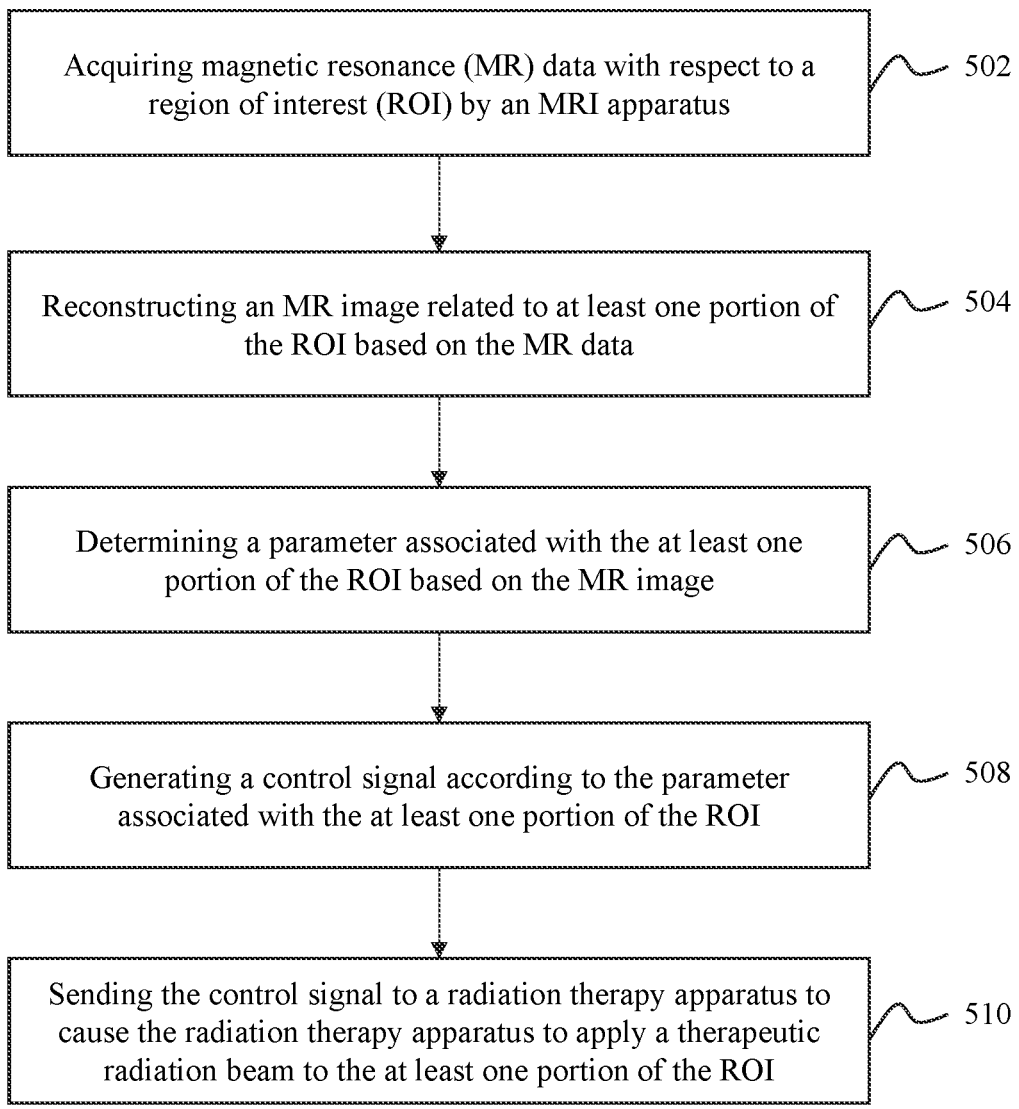
FIG. 5 is a flowchart illustrating an exemplary process for applying therapeutic radiation in a radiation therapy system according to some embodiments of the present disclosure.

FIG. 5 is a flowchart of an exemplary process for applying a therapeutic radiation by a radiation therapy system according to some embodiments of the present disclosure. In some embodiments, one or more operations of the process 500 illustrated in FIG. 5 may be implemented in the radiation therapy system 100 illustrated in FIG. 1. For example, the process 500 illustrated in FIG. 5 may be stored in the storage device 140 in the form of instructions, and invoked and/or executed by the one or more processing devices 120 illustrated in FIG. 1. For illustration purposes, the implement of the process 500 in the one or more processing devices 120 is described herein as an example. It should be noted that the process 500 can also be similarly implemented in the terminal device 150.

In 502, the one or more processing devices 120 may acquire magnetic resonance (MR) data with respect to a region of interest (ROI) by an MRI apparatus. The MR data may be MR signals received by an RF coil of the MRI apparatus (e.g., the MRI apparatus 200) from a subject.

In some embodiments, an ROI may refer to a region, e.g., a lesion, in a subject. For example, the ROI may be a region associated with a tumor of the subject. In some embodiments, the ROI may be a specific portion of the body, a specific organ, or specific tissue of the subject, such as the head, the brain, the neck, the body, shoulders, arms, the thorax, the heart, the stomach, blood vessels, soft tissue, knee, feet, etc., of the subject.

In 504, the one or more processing devices 120 may reconstruct an MR image of the ROI based on the MR data. The MR image may reflect a distribution of atomic nuclei inside the subject based on the MR data. Image reconstruction techniques of various types may be employed for reconstructing the MR image. Exemplary image reconstruction techniques may include Fourier reconstruction, constrained image reconstruction, regularized image reconstruction in parallel MRI, or the like, or a variation thereof, or any combination thereof.

In some embodiments, the MR image may be used to determine a radiation beam to be applied to a target region (e.g., at least one portion of the ROI). For example, the one or more processing devices 120 may determine the position of the at least one portion of the ROI and/or the dose of radiation to be delivered according to the MR image.

In some embodiments, it may take a long time (e.g., several minutes) to reconstruct an MR image of the ROI. It may be difficult to reconstruct an MR image of the ROI in real time during the radiation treatment if the ROI has a large size.

In some embodiments, in order to generate the MR image of the ROI during a relative short time period (e.g., several seconds), the one or more processing devices 120 may reconstruct an MR image of the at least one portion of the ROI. The MR image of the entire ROI (also referred to as primary MR image) may be reconstructed in advance (e.g., one day, two hours, half an hour, etc., before the radiation treatment). The processing device 120 may obtain MR data of the at least one portion of the ROI acquired by the MRI apparatus, and reconstruct an MR image of the at least one portion of the ROI during the radiation treatment (e.g., right before the radiation beam is applied on the at least one portion of the ROI). The processing devices 120 may combine MR image of the at least one portion of the ROI with the primary MR image. For example, the one or more processing devices 120 may use the MR image of the at least one portion of the ROI to replace a corresponding portion in the primary MR image. In this way, the primary MR image may be updated in a relatively short time period during the radiation treatment.

In 506, the one or more processing devices 120 may determine a parameter associated with the at least one portion of the ROI based on the MR image. In some embodiments, the parameter associated with the at least one portion of the ROI may include a size of a cross section of a lesion (e.g., a tumor) corresponding to the at least one portion of the ROI. In some embodiments, the parameter associated with the at least one portion of the ROI may indicate a shape of the cross section of the lesion.

In 508, the one or more processing devices 120 may generate a control signal according to the parameter associated with the at least one portion of the ROI. The control signal may be dynamically adjusted based on a plurality of MR images taken at different time points during the radiation treatment. In some embodiments, the control signal may include parameters associated with the radiation beam applied on the tumor. For example, the control signal may include the dosage of an X-ray beam, a duration of the radiation beam applied on the at least one portion of the ROI, etc. As another example, the control signal may include parameters of an MLC that shapes the radiation beam projected to the at least one portion of the ROI. In some embodiments, the control signal may include parameters associated with movements of one or more components of a radiation therapy apparatus (e.g., the radiation therapy apparatus 250). For example, the control signal may include a parameter associated with one or more positions of a radiation source of the radiation therapy apparatus (e.g., the target 256 of the radiation therapy apparatus 250). As another example, the control signal may include a parameter associated with a height and/or a position of a treatment table of the radiation therapy apparatus for properly positioning a patient so that the target region (e.g., a region corresponding to a lesion) in the patient may properly receive the radiation beam from the radiation therapy apparatus.

In 510, the one or more processing devices 120 may send the control signal to the radiation therapy apparatus to cause the radiation therapy apparatus to delivery the radiation beam to the at least one portion of the ROI. During the therapeutic radiation, the radiation source of the radiation therapy apparatus may rotate around a rotation axis. The dosage of the X-ray beam, a duration of the radiation beam applied to the at least one portion of the ROI, the shape of the MLC, and/or the position of the treatment table may be adjusted according to the control signal.

In some embodiments, as described above, the target region (e.g., the at least one portion of the ROI) may be determined according to the image data acquired from the MRI apparatus during the radiation treatment. Then the radiation beam may be generated and delivered by the radiation therapy apparatus to the target region. The dosage of the radiation beam and/or the position of the target region may be determined almost in real-time with the assistance of the MRI apparatus.

It should be noted that the above description is merely provided for the purposes of illustration, and not intended to limit the scope of the present disclosure. For persons having ordinary skills in the art, multiple variations or modifications may be made under the teachings of the present disclosure. For example, the primary MR image may be obtained from a storage device in the radiation therapy system 100, such as the storage device 140. As another example, the parameter associated with the at least one portion of the ROI determined based on the MR image may also include a position of the at least one portion of the ROI in a coordinate system (e.g., the coordinate system 160 as illustrated in FIG. 1). However, those variations and modifications do not depart from the scope of the present disclosure.

FIGS. 6A through 6F illustrate various views an exemplary therapeutic apparatus and a trajectory of an electron beam generated by the exemplary therapeutic apparatus according to some embodiments of the present disclosure. The therapeutic apparatus 600 may include an MRI apparatus and a radiation therapy apparatus. The MRI apparatus may be configured to generate MR data of an ROI of a subject. The radiation therapy apparatus may be configured to apply a radiation beam to at least one portion of the ROI based on an MR image reconstructed based on the MR data.

Figure 6A:
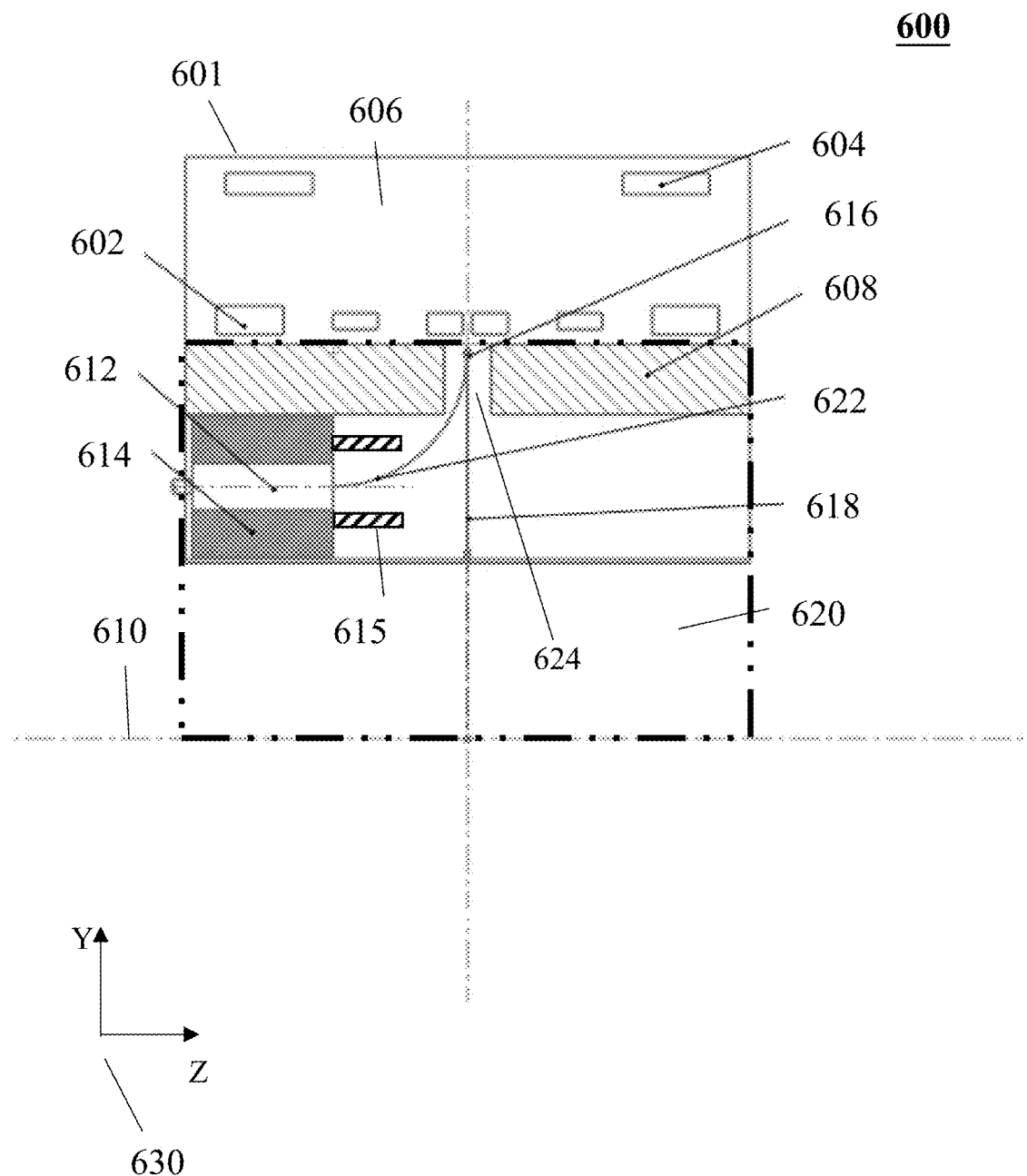
FIGS. 6A through 6F illustrate various views of an exemplary therapeutic apparatus and a trajectory of an electron beam generated by the exemplary therapeutic apparatus according to some embodiments of the present disclosure.
Figure 6B:
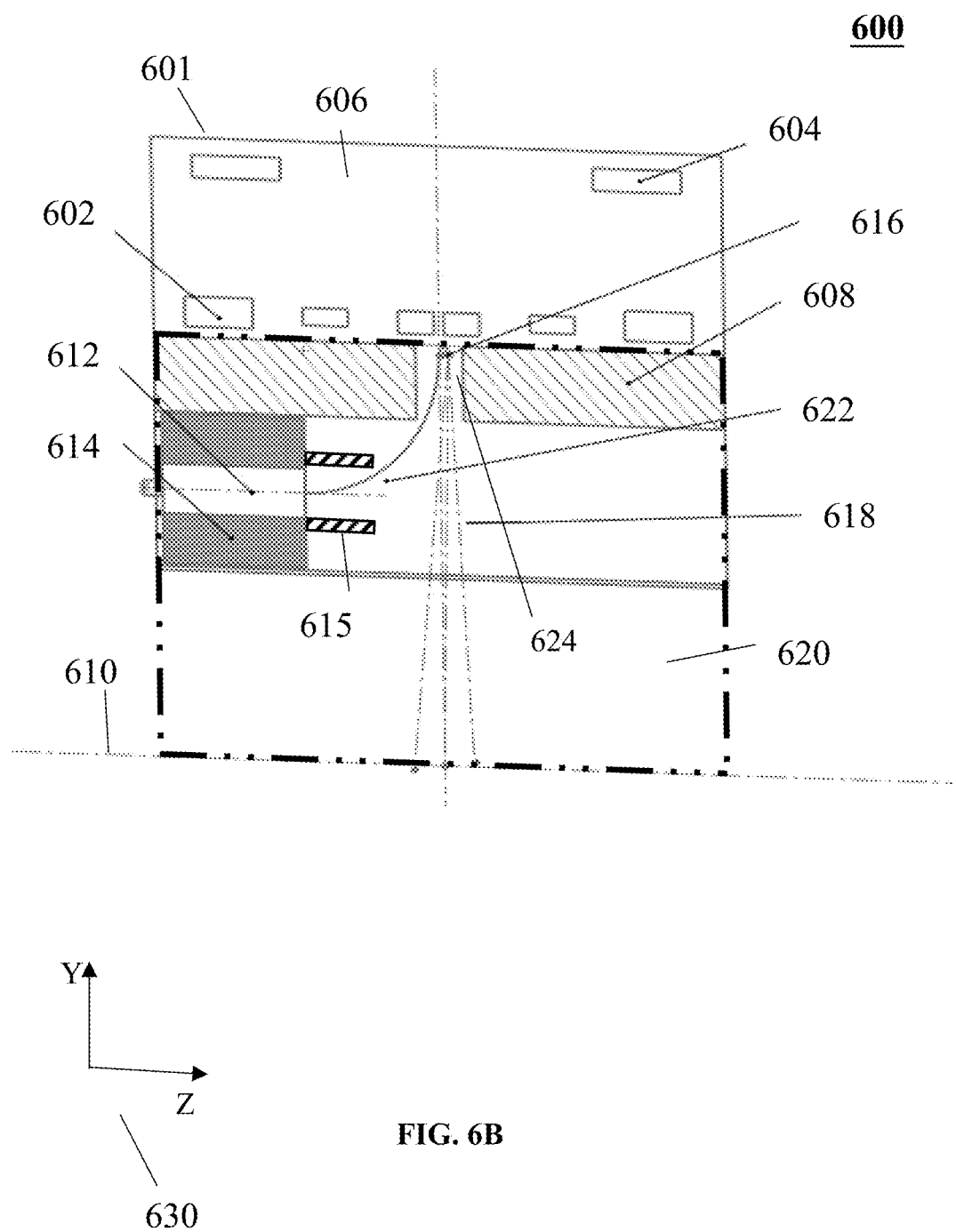
Figure 6C:
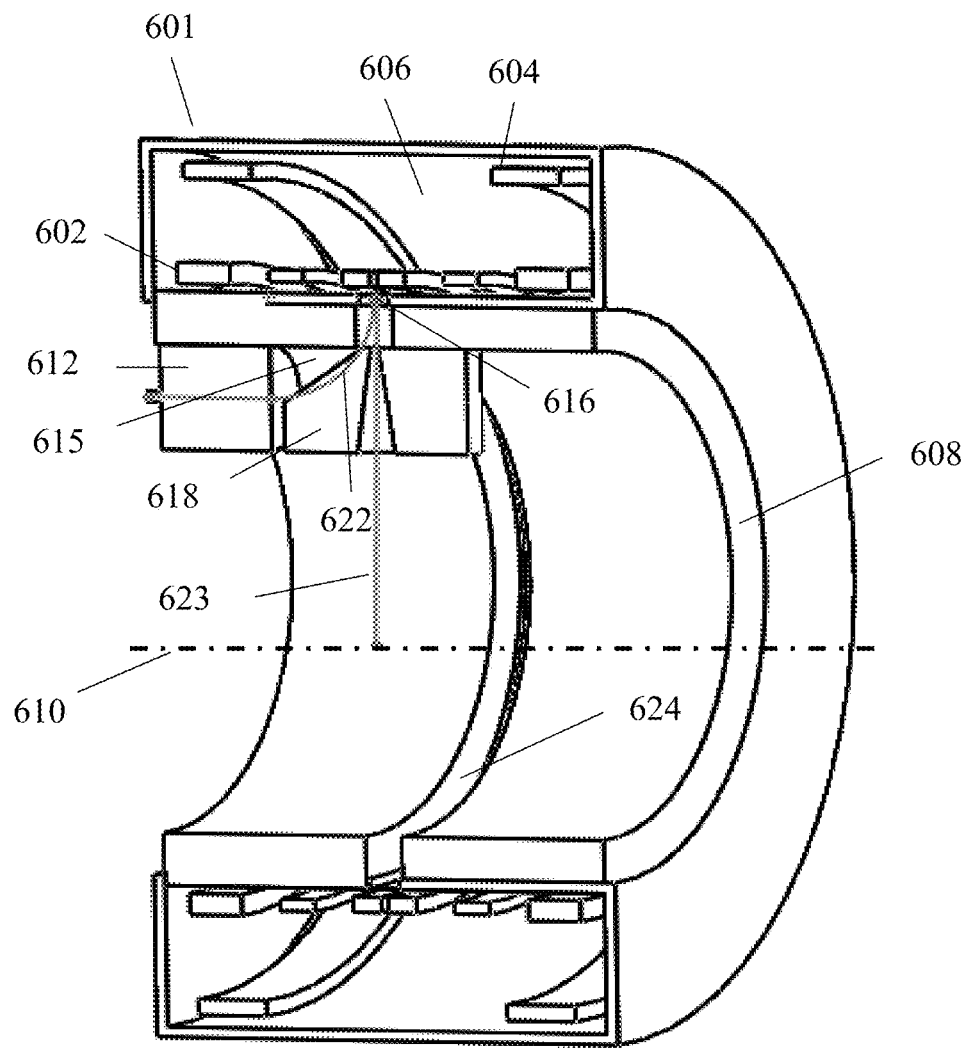

FIGS. 6A and 6B illustrate a half of a cross-section of the therapeutic apparatus according to some embodiments of the present disclosure. FIG. 6C illustrates a three-dimensional (3D) structure of the therapeutic apparatus according to some embodiments of the present disclosure. In some embodiments, the 3D structure shown in FIG. 6C may be formed by sectioning the therapeutic apparatus 600 with a sectional plane (e.g., the Y-Z plane or a plane parallel to the Y-Z plane as illustrated in FIG. 6C) and viewing the therapeutic apparatus 600 along a negative direction of the X axis. In some embodiments, the cross-section as illustrated in FIGS. 6A and 6B may be formed in the sectional plane (the Y-Z plane as illustrated in FIGS. 6A and 6B)). FIG. 6A is a front view of a half of the cross-section of the therapeutic apparatus 600. FIG. 6B is an oblique view of the half of the cross-section of the therapeutic apparatus 600.

Figure 6D:
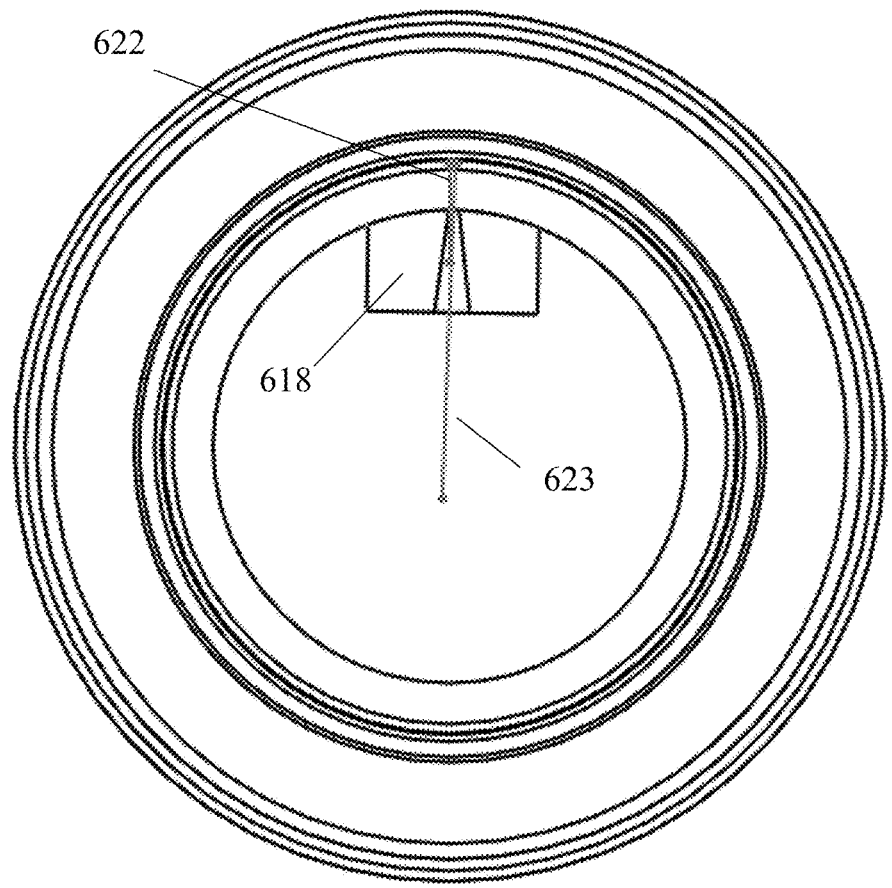
Figure 6E:
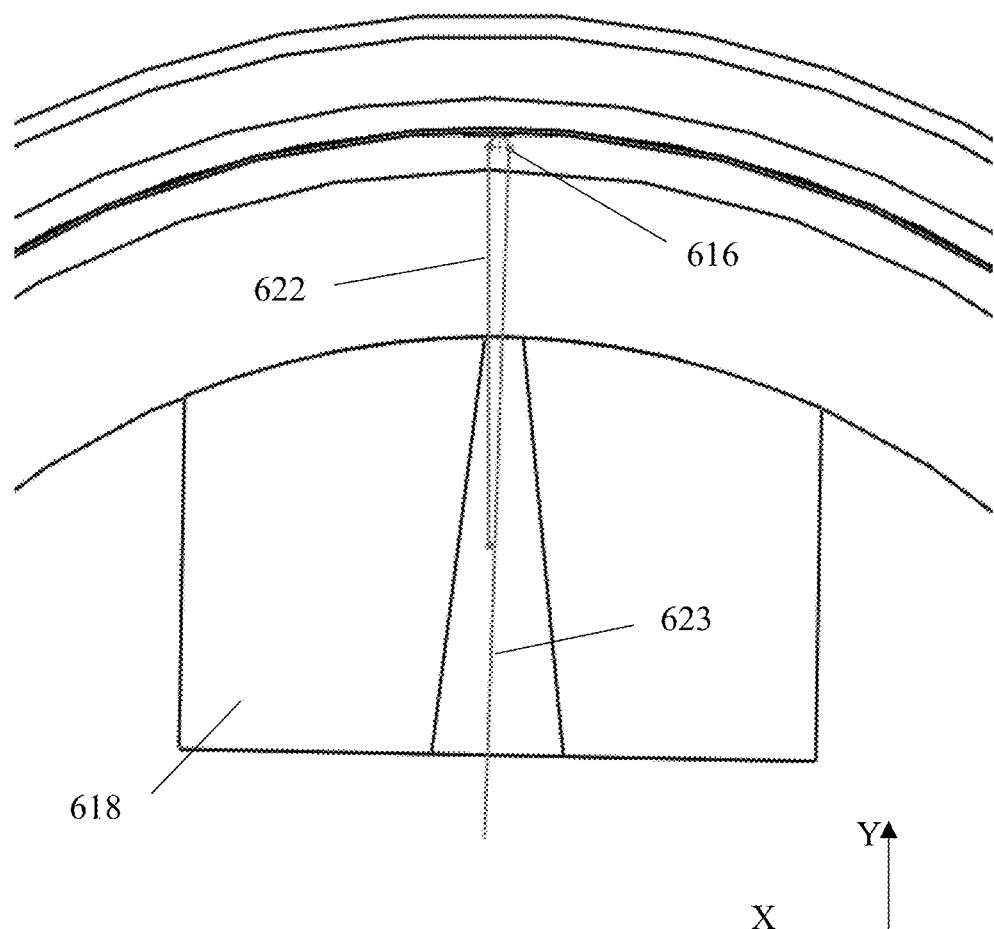
Figure 6F:
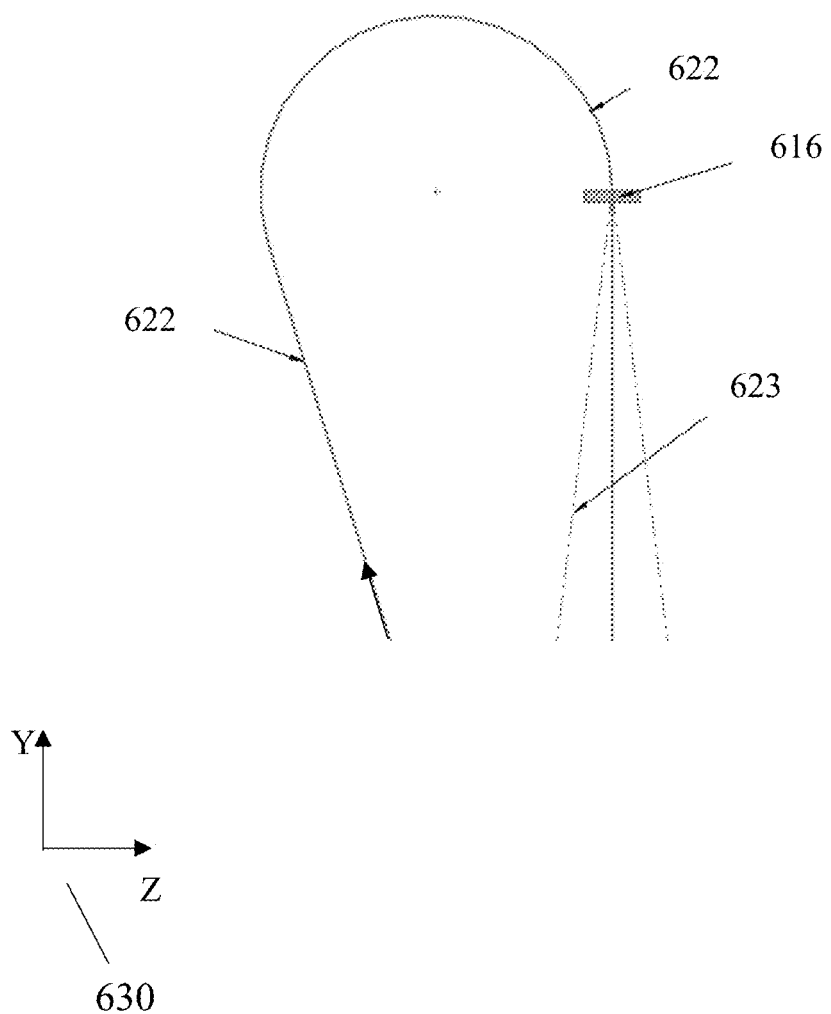

FIG. 6D illustrates a side view of the therapeutic apparatus 600 according to some embodiments of the present disclosure. In some embodiments, the side view of the therapeutic apparatus 600 may be formed by viewing the therapeutic apparatus 600 along a negative direction of the Z axis with reference to a coordinate system 630. FIG. 6E is an enlarged view of a portion of the therapeutic apparatus including an illustration of a trajectory of an electron beam generated by the therapeutic apparatus 600 according to some embodiments of the present disclosure. FIG. 6F is a schematic diagram of the trajectory of the electron beam generated by the therapeutic apparatus 600 according to some embodiments of the present disclosure. Illustratively, the therapeutic apparatus 600 are described in detail below with reference to FIGS. 6A through 6F.

In some embodiments, the MRI apparatus may be or include a permanent magnet MRI scanner, a superconducting electromagnet MRI scanner, or a resistive electromagnet MRI scanner, etc., according to types of a magnetic body of the MRI apparatus. In some embodiments, the MRI apparatus may be or include a high-field MRI scanner, a mid-field MRI scanner, and a low-field MRI scanner, etc., according to an intensity of a magnetic field generated by the magnetic body of the MRI apparatus. In some embodiments, the MRI apparatus may be of a closed-bore (cylindrical) type, an open-bore type, or the like. The MRI apparatus may include a magnetic body 601.

The magnetic body 601 may have a shape of an annulus around an axis 610 represented by a light dot-dashed line as illustrated in FIGS. 6A through 6C. The axis 610 may be parallel to the Z direction of the coordinate system 630. An inner surface of the magnetic body 601 may form a bore 620, which is represented by a rectangle box composed of thick double-dot-dash lines as illustrated in FIGS. 6A and 6B. The magnetic body 601 may generate a magnetic field. The magnetic body 601 may be of various types including, for example, a permanent magnet, a superconducting electromagnet, a resistive electromagnet, etc. The following descriptions are provided that the magnetic body 601 may be a superconducting electromagnet. It is understood that it is merely for illustration purposes, and not intended to be limiting.

As shown in FIGS. 6A through 6C, the magnetic body 601 may include a plurality of main magnetic coils 602, a plurality of shielding magnetic coils 604, and a cryostat 606.

In some embodiments, the plurality of main magnetic coils 602 and the plurality of shielding magnetic coils 604 may be accommodated in the cryostat 606. The cryostat 606 may contain a coolant. The coolant may include, for example, liquid helium. The plurality of main magnetic coils 602 and the plurality of shielding magnetic coils 604 may be at least partially immerged in the coolant in the cryostat 606. The coolant may maintain the plurality of main magnetic coils 602 and the plurality of shielding magnetic coils 604 at a low temperature (e.g., 4.2 K) such that the plurality of main magnetic coils 602 and the plurality of shielding magnetic coils 604 may maintain a superconducting state.

The cryostat 606 may have a shape of an annulus with an axis 610. In some embodiments, an outline of the cryostat 606 may at least partially coincide with that of the magnetic body 601. The plurality of main magnetic coils 602 may be arranged around the axis 610 in the cryostat 606. The plurality of main magnetic coils 602 may generate a uniform main magnetic field (e.g., a static magnetic field $B_0$) within a specific region (e.g., the bore 620) when the plurality of main magnetic coils 602 carry an electric current (e.g., the electric current flows along a positive direction of the Z axis). The direction of the main magnetic field may be parallel to the axis 610 in the bore 620.

The plurality of shielding magnetic coils 604 may shield the magnetic field generated by the plurality of main magnetic coils 602 in a region outside the MRI apparatus. In some embodiments, the plurality of shielding magnetic coils 604 may carry an electric current along a direction (e.g., a negative direction of the Z axis) that is opposed to the direction of the electric current on the plurality of main magnetic coils 602. A magnetic field generated by the plurality of shielding magnetic coils 604 may reduce or cancel the magnetic field generated by the plurality of main magnetic coils 602 in the region outside the MRI apparatus. In some embodiments, the plurality of shielding magnetic coils 604 may be annular coils arranged along the axis 610, coaxially with the plurality of main magnetic coils 602. In some embodiments, the plurality of shielding magnetic coils 604 may be of at a larger radius from the axis 610 than the plurality of main magnetic coils 602.

The MRI apparatus may further include one or more gradient coils 608. The one or more gradient coils 608 may generate magnetic field gradients to be superposed on the main magnetic field $B_0$ in the X, Y, and/or Z directions. In some embodiments, the one or more gradient coils 608 may include at least one X coil, at least one Y coil, and/or at least one Z coil, etc. An X coil may be energized to generate a gradient field in the X direction. A Y coil may be energized to generate a gradient field in the Y direction. A Z coil may be energized to generate a gradient field in the Z direction. Merely by way of example, the at least one Z coil may be designed based on a circular (Maxwell) coil, and the at least one X coil and the at least one Y coil may be designed based on a saddle (Golay) coil.

In some embodiments, the gradient magnetic fields may include a slice-selection gradient field corresponding to the Z direction, a phase encoding (PE) gradient field corresponding to the Y direction, a readout (RO) gradient field corresponding to the X direction, etc. The gradient magnetic fields in different directions may be used to encode spatial information of MR signals. In some embodiments, the gradient magnetic fields may also be used to perform at least one function of flow encoding, flow compensation, flow dephasing, or the like, or any combination thereof.

The one or more gradient coils 608 may be located in the bore 620. In some embodiments, the one or more gradient coils 608 may be arranged on or close to an inner surface of the magnetic body 601. In some embodiments, one or more gradient coils 608 may be configured as at least one gradient coil set. Each gradient coil set may include at least one gradient coil (e.g., an X coil, a Y coil, and/or a Z coil). In some embodiments, a gradient coil set may have an annular structure around the axis 610. The at least one gradient coil set may be arranged on or close to the inner surface of the magnetic body 601 in a circumferential direction of the at least one gradient coil set. The at least one gradient coil set or a part of thereof may be spaced continuously or apart from each other in a longitudinal direction of the at least one gradient coil set (i.e., the Z direction). A distance between at least two pairs of neighboring gradient coil sets may be the same or different when the at least one gradient coil set is spaced apart from each other. The one or more gradient coils 608 may be energized at a room temperature rather than a low temperature, such as 4.2 K.

The radiation therapy apparatus may include a linear accelerator 612, a radiation shielding component 614, a deflection device 615, a target 616, and a treatment head 618.

The linear accelerator 612 may accelerate electrons to form an electron beam of a certain energy level. In some embodiments, the linear accelerator 612 may accelerate electrons using microwave technology. In some embodiments, the linear accelerator 612 may be operably coupled to a microwave device (not shown in the figure). The microwave device may be configured to accelerate the electrons in the linear accelerator 612. In some embodiments, the linear accelerator 612 may be operably coupled to the microwave device through a rotation waveguide. The rotation waveguide may enable the microwave device to stand stationary relative to the MRI apparatus when the linear accelerator 612 rotates around the axis 610 during the radiation treatment of the subject. In some embodiments, the microwave device may also rotate around the axis 610 along with the linear accelerator 612 during the radiation treatment of the subject.

The linear accelerator 612 may be located in the bore 620 formed by the inner surface of the magnetic body 601. In some embodiments, a length direction of the linear accelerator 612 may be parallel with the axis 610. More specifically, the linear accelerator 612 may include an accelerating tube. The accelerating tube may provide a linear path for accelerating the electrons. An axis of the accelerating tube may be parallel to the axis 610 (or the Z direction). In such embodiments, the moving direction of the electrons in the linear accelerator 612 may be parallel with the direction of the main magnetic field Bo, and the acceleration of the electrons in the linear accelerator 612 may be (substantially) spared from the effect of the main magnetic field Bo. Thus, the linear accelerator 612 may not need a magnetic shielding when the length direction of the linear accelerator 612 is parallel with the axis 610.

In some embodiments, the linear accelerator 612 may be arranged inside the one or more gradient coils 608 (i.e., within an opening formed by inner surfaces of one or more gradient coils 608). As illustrated in FIGS. 6A through 6C, the linear accelerator 612 may be located closer to the axis 610 than the one or more gradient coils 608 according to the half of the cross-section of the therapeutic apparatus 600. In some embodiments, the linear accelerator 612 may be arranged at any suitable position within the opening formed by the inner surfaces of the one or more gradient coils 608. For example, the linear accelerator 612 may be attached or close to (e.g., having a distance of 1 centimeter, 2 centimeter, 5 centimeter etc.) an inner surface of the opening. As another example, the linear accelerator 612 may be arranged on the axis 610 (i.e., a center line of the linear accelerator 612 may coincide with the axis 610).

In some embodiments, the linear accelerator 612 may be disposed at or close to an end of the bore 620 in the Z direction. The linear accelerator 612 may include a first end at which the acceleration of the electrons in the electron beam starts and a second end at which the electron beam emits outwards along the Z direction. The bore 620 may include a first end at a back side and a second end at a front side of the therapeutic apparatus 600. The front side and the back side may be two sides of the therapeutic apparatus when viewed as illustrated in FIG. 1 along the negative direction of the Z axis, respectively. The front side of the therapeutic apparatus is visible in FIG. 1, while the back side is invisible in FIG. 1.

In some embodiments, the first end of the linear accelerator 612 may be aligned with the first end or the second end of the bore 620. In some embodiments, the first end of the linear accelerator 612 may be close to the first end or the second end of the bore 620. Merely for illustration purposes, a distance between the first end of the linear accelerator 612 and the first end or the second end of the bore 620 may be 0 centimeters, 5 centimeters, 10 centimeters, 20 centimeters, 50 centimeters, etc. In some embodiments, the distance between the first end of the linear accelerator 612 and the first end or the second end of the bore 620 may be adjustable. For example, the linear accelerator 612 may be fixed on a moving platform (not shown in the figure). The moving platform may be movable along the Z direction. The distance between the first end of the linear accelerator 612 and the first end or the second end of the bore 620 may be adjusted by controlling the movement of the moving platform. In some embodiments, the movement of the moving platform may be realized by a sliding structure, for example, a sliding rail.

The linear accelerator 612 (e.g., an accelerating tube of the linear accelerator 612) may be at least partially surrounded by a radiation shielding component 614. The radiation shielding component 614 may protect the subject and/or one or more components of the MRI apparatus from the radiation produced by the linear accelerator 612. In some embodiments, the radiation shielding component 614 may provide a cavity coaxial with the longitudinal direction of the linear accelerator 612, with at least one end being open to let through the electron beam emitted from the linear accelerator 612. In some embodiments, the radiation shielding component 614 may have an annular structure surrounding the linear accelerator 612. A length of the radiation shielding component 614 in the Z direction may be equal to or greater than a length of the linear accelerator 612.

The radiation shielding component 614 may be made of a material that absorbs the radiation produced by the radiation beam of the linear accelerator 612 so as to provide radiation shielding for the subject and/or the one or more components of the MRI apparatus. Exemplary materials that absorb radiation may include a material for absorbing a photon ray and/or a material for absorbing a particle ray (e.g., a neutron ray). The material for absorbing a photon ray may include steel, aluminum, lead, tungsten, etc., or an alloy thereof, or a combination thereof. The material for absorbing a neutron ray may include boron, graphite, etc., or an alloy thereof, or a combination thereof.

The target 616 may produce a radiation beam for radiation treatment of the subject (e.g., the at least portion of the ROI of the subject) when the accelerated electron beam collides on the target 616. For example, the electron beam emitted from the linear accelerator 612 may be deflected onto the target 616 to generate X-rays at a high energy level according to the Bremsstrahlung effect. In some embodiments, the target 616 may be made of a material including aluminum, copper, silver, tungsten, or the like, or an alloy thereof, or any combination thereof. Alternatively, the target 616 may be made of a composite material including tungsten and copper, tungsten and silver, tungsten and aluminum, or the like, or an alloy thereof, or any combination thereof. In some embodiments, the target 616 may be a circular plate having a relatively small thickness (e.g., several micrometers to dozens of micrometers).

In some embodiments, the one or more gradient coils 608 may be split gradient coils. Each split gradient coil may include at least one gradient coil. In some embodiments, a split gradient coil may have an annular structure around the axis 610. In some embodiments, the split gradient coils may be spaced apart from each other along the Z direction. Merely for illustration purposes, the one or more gradient coils 608 may be configured as two split gradient coils around the axis 610 as illustrated in FIGS. 6A through 6C. The two split gradient coils may be spaced apart, thus forming an annular gap 624. A depth of the annular gap 624 may equal to a thickness of a gradient coil. In some embodiments, the target 616 may be located in the annular gap 624 between the two split gradient coils. In some embodiments, the target 616 may be located at a central position of the gap 624.

It should be noted that the position of the target 616 is merely provided for illustration purposes, and not intended to be limiting. In some alternative embodiments, the target 616 may be located at any suitable position in the bore 620. For example, the target 616 may be located inside the opening formed by inner surfaces of the one or more gradient coils 608. In some embodiments, an annular recess may be set on the inner surface of the cryostat 606. The target 616 may be disposed in the annular recess of the cryostat 606.

The deflection device 615 may be configured to deflect the electron beam emitted from the linear accelerator 612 towards the target 616 along a trajectory 622. Exemplary deflection devices may include a microwave cavity, a deflection magnet (e.g., a permanent magnet, an electromagnet, etc.), a magnetic lens, or the like, or any combination thereof. In some embodiments, the deflection device 615 may include at least one deflection magnet. The at least one deflection magnet may be a permanent magnet, an electromagnet, etc. In some embodiments, the deflection device 615 may be implemented by a permanent magnet if the energy of the electron beam emitted from the linear accelerator 612 is fixed.

The trajectory 622 of the electron beam may be shown in FIGS. 6D through 6F in detail. According to FIGS. 6D through 6F, the electron beam emitted from the linear accelerator 612 may be deflected to an outer surface of the target 616 along the curved trajectory 622. The outer surface of the target 616 may refer to a surface of the target 616 that has a larger distance from the axis 610.

Since the electrons emitted from an outlet of the linear accelerator 612 is within the main magnetic field $B_0$ generated by the plurality of main magnetic coils 602, the deflection device 615 may be properly designed such that the electron beam may (substantially) vertically (or referred to as substantially perpendicularly) collide onto the target 616 after travelling along the trajectory 622 under a combined action of both the main magnetic field $B_0$ generated by the plurality of main magnetic coils 602 and a deflection magnetic field generated by the deflection device 615. In some embodiments, the radiation therapy apparatus may further include one or more correction coils along the trajectory 622 of the electron beam. The one or more correction coils may be configured to correct the trajectory 622 of the electron beam so that the electron beam collides onto the target 616 substantially vertically.

In some embodiments, the deflection device 615 may include at least one arc-shaped deflection channel. The arc-shaped deflection channel may be covered or surrounded by a magnetic shielding material that (substantially) shields the main magnetic field $B_0$. The electron beam may be deflected towards the target 616 in the at least one arc-shaped deflection channel within the deflection magnetic field generated by the deflection device 615.

The radiation beam from the target 616 may pass through the treatment head 618. The treatment head 618 may be configured to deliver radiation beam to a target region of the subject from a specific angle. The treatment head 618 may include a collimator (not shown in the figure) to reshape the radiation beam. For example, the collimator may adjust an irradiating shape, an irradiating area, etc., of the radiation beam by blocking a specific portion of the radiation beam. In some embodiments, the collimator may include a primary collimator, a flattening filter, and at least one secondary collimator. In some embodiments, the collimator may be an MLC. The MLC may include a plurality of individual leaves moving independently in and out of the path of the radiation beam so as to block a specific portion of the radiation beam. The shape of the radiation beam may vary when the plurality of individual leaves move in and out, forming different slots that approximates a cross-sectional view of the target region (e.g., the at least one portion of the ROI) viewed along the radiation beam. In some embodiments, the MLC may include one or more layers of leaves. For example, the MLC may have only one layer of leaves and the height of the MLC along the axis of the radiation beam may be between 7 and 10 centimeters. As another example, the MLC may include two layers and the height of the MLC may be at least 15 centimeters. The leaves of the MLC may be made of at least one high atomic numbered material (e.g., tungsten).

The treatment head 618 may be placed anywhere on a path 623 of the radiation beam. For example, the treatment head 618 may be placed close to the target 616. As another example, the treatment head 618 may be placed at a relatively long distance away from the target 616.

In some embodiments, one or more of the deflection device 615, the target 616, and the treatment head 618 may stay fixed relative to the linear accelerator 612, thus rotating together with the linear accelerator 612 around the axis 610 during the radiation treatment of the subject. In some embodiments, the linear accelerator 612, the deflection device 615, the target 616, and the treatment head 618 may be accommodated in a housing of the radiation therapy apparatus. In some embodiments, the linear accelerator 612, the deflection device 615, the target 616, and the treatment head 618 may stay relatively fixed via a physical structure (e.g., mechanical structures such as one or more rods, one or more plate, not shown), a glue, or the like, or a combination thereof. The housing may have any suitable shape in its cross-section, such as an annulus, an arc, etc. In some embodiments, the one or more gradient coils 608 may also be accommodated in the housing. The housing may be connected to the gantry. For example, the housing may be connected to the gantry via mechanical joints. The gantry may be capable of rotating around the axis 610. Then the components of the radiation therapy apparatus in the housing may rotate around the axis 610 along with the gantry during the radiation treatment of the subject, and thus may enable the radiation beam to be emitted to the target region of the subject from any one of circumferential positions along the circumference of or defined by the therapeutic apparatus 600.

In such embodiments, many components of the radiation therapy apparatus (e.g., the linear accelerator 612, the deflection device 615, the target 616, and the treatment head 618) may be disposed in the bore 620. A source-to-axis distance (SAD) from the target 616 of the radiation therapy apparatus to the rotation axis of the gantry (i.e., the axis 610) may be smaller than conventional MRI-RT systems, thereby improving a dose rate of the radiation beam, and enhancing the therapeutic effect of the target region of the subject.

Figure 7A:
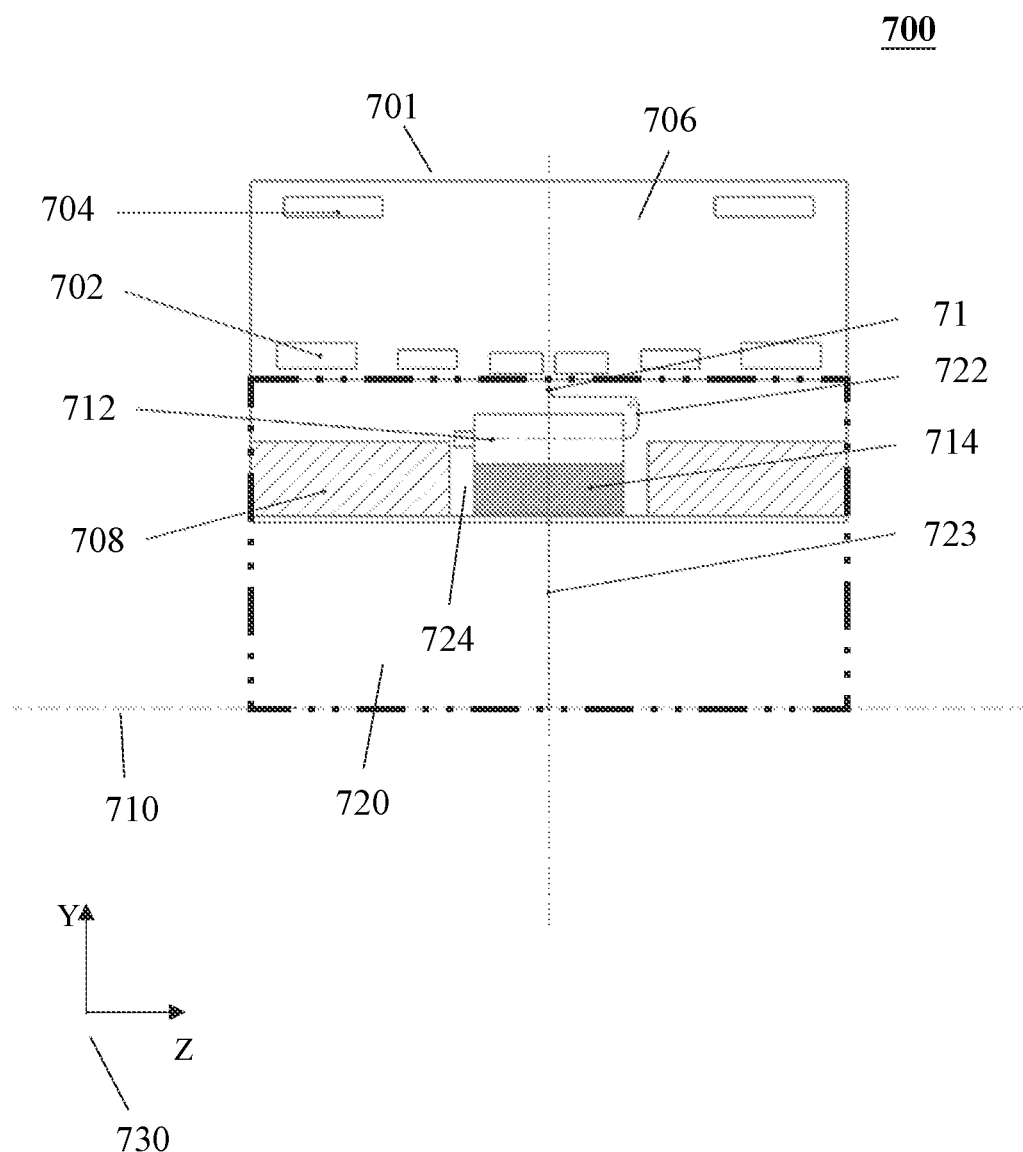
FIGS. 7A through 7D illustrate various views of an exemplary therapeutic apparatus according to some embodiments of the present disclosure.
Figure 7B:
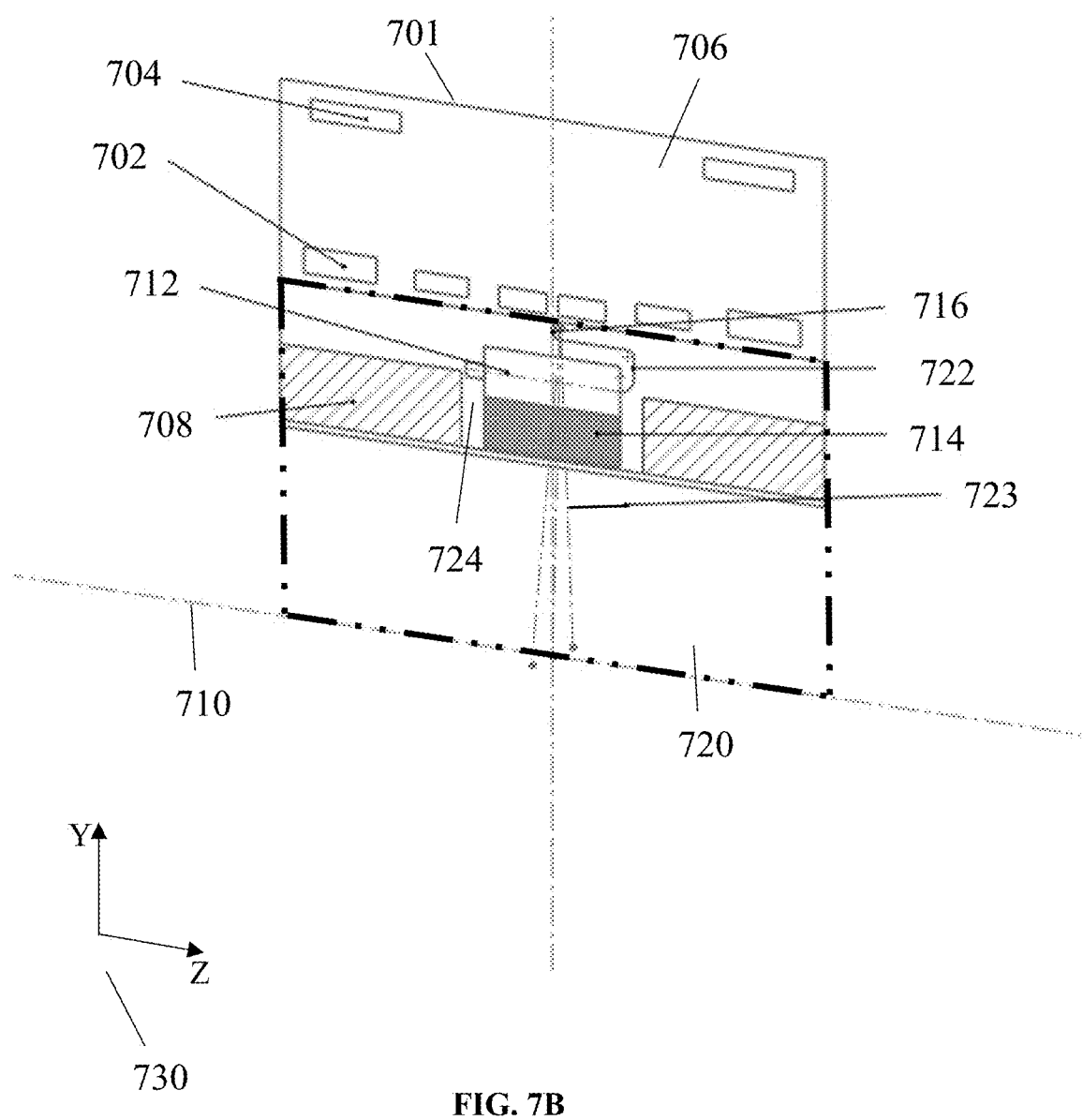
Figure 7C:
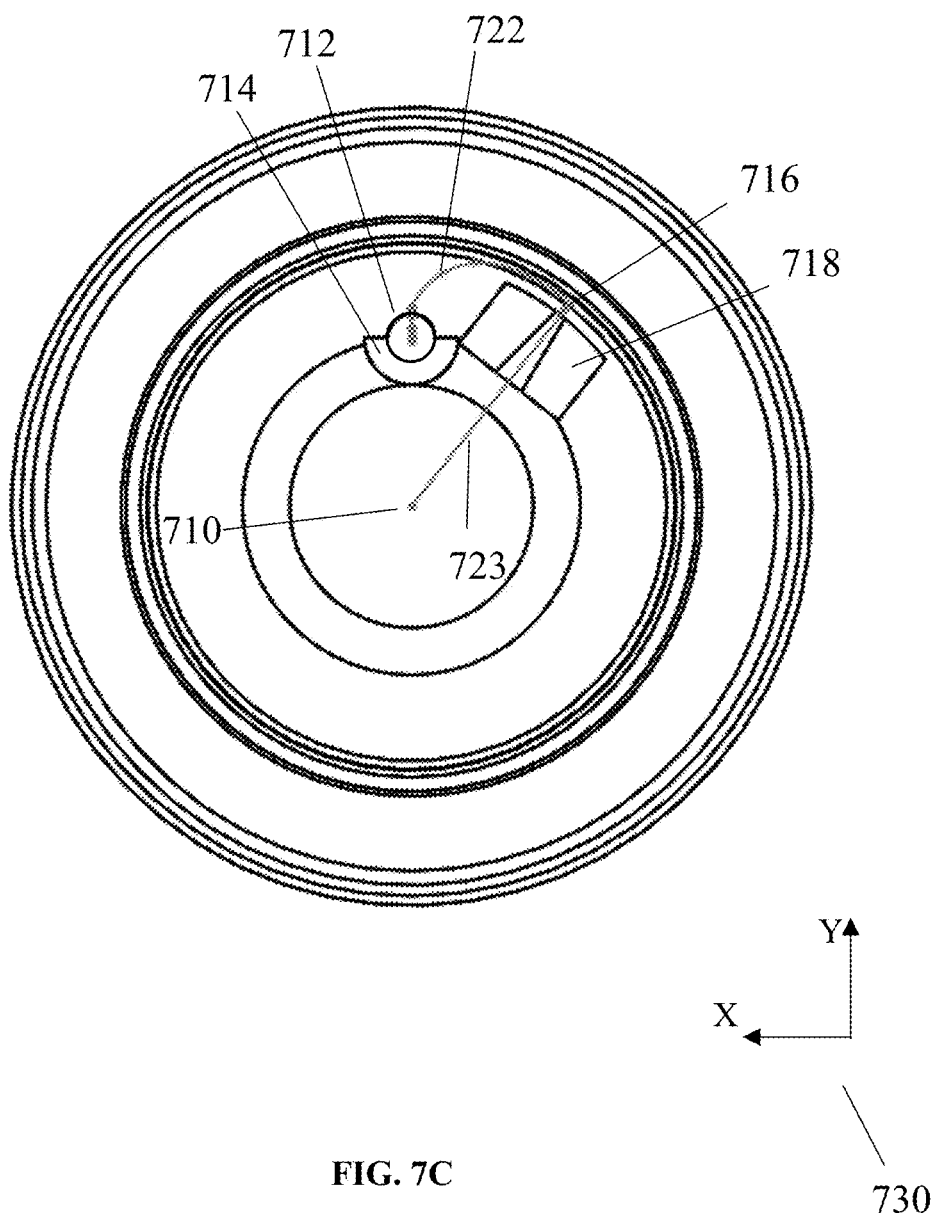
Figure 7D:
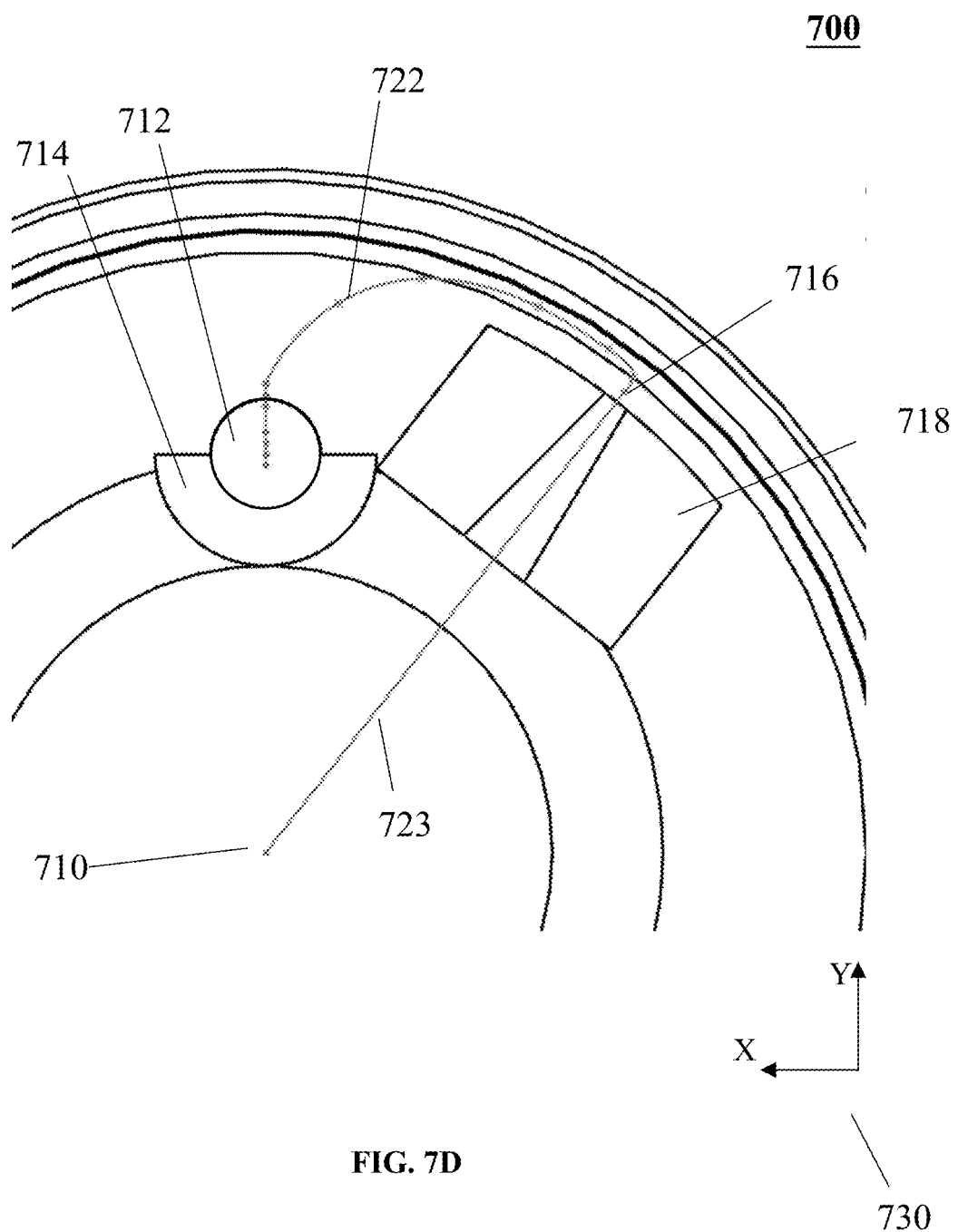

FIGS. 7A through 7D illustrate various views of an exemplary therapeutic apparatus according to some embodiments of the present disclosure. The therapeutic apparatus 700 may include an MRI apparatus and a radiation therapy apparatus similar to those described in connection with FIGS. 6A-6F. FIGS. 7A and 7B illustrate a half of a cross-section of the therapeutic apparatus 700 according to some embodiments of the present disclosure. FIG. 7A is a front view of the half of the cross-section of the therapeutic apparatus 700. FIG. 7B is an oblique view of the half of the cross-section of the therapeutic apparatus 700. FIG. 7C illustrates a side view of the therapeutic apparatus 700 according to some embodiments of the present disclosure. In some embodiments, the side view of the therapeutic apparatus 700 may be formed by viewing the therapeutic apparatus 700 along a negative direction of the Z axis with reference to a coordinate system 730. FIG. 7D is an enlarged view of a portion of the therapeutic apparatus 700 including an illustration of a trajectory of an electron beam generated by the therapeutic apparatus according to some embodiments of the present disclosure. The therapeutic apparatus 700 may be described below in combination with both FIG. 7A and FIG. 7B.

The MRI apparatus may include a magnetic body 701 and one or more gradient coils 708. The magnetic body 701 may include a plurality of main magnetic coils 702, a plurality of shielding magnetic coils 704, and a cryostat 706. In some embodiments, the plurality of main magnetic coils 702, the plurality of shielding magnetic coils 704, the cryostat 706, and the one or more gradient coils 708 may be coaxially or concentrically arranged around an axis 710. The radiation therapy apparatus may include a linear accelerator 712, a radiation shielding component 714, a deflection device (not shown in the figure), a target 716, and a treatment head 718.

Comparing with the one or more components of the therapeutic apparatus 600, a position of the linear accelerator 712 as illustrated in FIGS. 7A and 7B may be different from the position of the linear accelerator 612 as illustrated in FIGS. 6A and 6B. In some embodiments, the linear accelerator 712 may be arranged between two neighboring split gradient coils. Each split gradient coil may include at least one gradient coil. In some embodiments, a split gradient coil may have an annular structure around the axis 710. In some embodiments, the linear accelerator 712 may be arranged at or close to a mid-point of a bore 720 formed by the magnetic body 701 (or the cryostat 706 has a shape of an annulus) in a length direction of the bore 720. As illustrated in FIGS. 7A and 7B, the one or more gradient coils 708 may be configured as two split gradient coils. The two split gradient coils may be spaced apart from each other, thus forming a gap 724. In some embodiments, the gap 724 between the two split gradient coils may be greater than a length of the linear accelerator 712. The linear accelerator 712 may be located in the gap 724 between the two split gradient coils. A length direction of the linear accelerator 712 may be parallel with the axis 710. By arranging the linear accelerator 712 in the gap 724 between the two split gradient coils, a thickness of a housing accommodating the linear accelerator 712, the radiation shielding component 714, the deflection device 715, the target 716, and the treatment head 718, which substantially equals to a distance from the target 716 to an outer surface of the radiation shielding component 714 in the Y direction, may be greatly reduced. If the space for placing the subject in the bore 720 remains constant, a circumferential size of the therapeutic apparatus 700 may be reduced relative to the therapeutic apparatus 600.

The target 716 may be placed above the linear accelerator 712 in terms of the cross-section of the therapeutic apparatus 700 as illustrated in FIGS. 7A and 7B (i.e., a distance between the target 716 and the axis 710 may be greater than the distance between the linear accelerator 712 and the axis 710).

A trajectory 722 of the electron beam is shown in FIGS. 7C and 7D. According to FIGS. 7C and 7D, the electron beam emitted from the linear accelerator 712 may be deflected to an outer surface of the target 716 along the curved trajectory 722. The outer surface of the target 716 may refer to a surface of the target 716 that has a larger distance from the axis 710. The linear accelerator 712 and the target 716 may correspond to different circumferential angles. As used herein, a circumferential angle is an angle in the X-Y plane with reference to the coordinate system 730. In some embodiments, the circumferential angle may be defined with reference to the axis 710 in the bore 720 and a negative direction of the X axis. For example, the linear accelerator 712 may correspond to a circumferential angle of 90 degrees. Merely for illustration, the linear accelerator 712 may be located at a first position corresponding to a first circumferential angle of the bore 720. The target 716 may be located at a second position corresponding to a second circumferential angle of the bore 720. The first circumferential angle is different from the second circumferential angle.

The deflection device 715 may be designed such that the electron beam emitted from the linear accelerator 712 may (substantially) vertically collide onto the target 716 after travelling along the trajectory 722 under a combined action of both a main magnetic field Bo generated by the plurality of main magnetic coils 702 and a deflection magnetic field generated by the deflection device. In some embodiments, the deflection device 715 may include at least one arc-shaped deflection channel. The arc-shaped deflection channel may be covered or surrounded by a magnetic shielding material that (substantially) shields the main magnetic field Bo generated by the plurality of main magnetic coils 702. The electron beam may be deflected towards the target 716 in the at least one arc-shaped deflection channel within the deflection magnetic field generated by the deflection device. A radiation beam may be generated after the electron beam collides onto the target 716. The radiation beam from the target 716 may pass through the treatment head 618, and be delivered to a target region of the subject from a specific angle.

The linear accelerator 712 may be away from on a path 723 of the radiation beam from the target 716 to the target region of the subject. In some embodiments, a line connecting the target region of the subject and the target 716 may have an angle with another line connecting the target region of the subject and a center of the linear accelerator 712. The angle may be larger than a threshold, for example, 5 degrees, 10 degrees, 15 degrees, 20 degrees, 30 degrees, etc.

Accordingly, the radiation shielding component 714 that facilitates radiation shielding for the linear accelerator 712 (e.g., an accelerating tube of the linear accelerator 612) may vary. The radiation shielding component 714 may protect the subject and/or one or more components of the MRI apparatus from the radiation produced by the linear accelerator 712. In some embodiments, the radiation shielding component 714 may surround a portion of the linear accelerator 712. The surrounded portion of the linear accelerator 712 may be closer to the axis 710. In some embodiments, the radiation shielding component 614 may have a semi-annular structure surrounding a lower portion of the linear accelerator 612 in terms of the cross-sectional view of the therapeutic apparatus 700 as illustrated in FIGS. 7A and 7B (i.e., a semi-annular portion of the linear accelerator 712 be closer to the axis 710). A length of the radiation shielding component 714 in the Z direction may be equal to or greater than a length of the linear accelerator 712.

It should be noted that the above description is merely provided for the purposes of illustration, and not intended to limit the scope of the present disclosure. For persons having ordinary skills in the art, multiple variations or modifications may be made under the teachings of the present disclosure. For example, an annular recess may be set on the inner surface of the cryostat 606. The linear accelerator 712 and the target 716 may be disposed in the circular or annular recess of the cryostat 706. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A radiation therapy system, comprising:
   a magnetic resonance imaging apparatus configured to acquire MRI data with respect to a region of interest of a subject, the MRI apparatus including a magnetic body; and
   a radiation therapy apparatus configured to apply a radiation beam to at least one portion of the ROI, the radiation therapy apparatus including:
      a linear accelerator configured to accelerate electrons to produce the radiation beam, the linear accelerator being located in a bore formed by an inner surface of the magnetic body, and a length direction of the linear accelerator being parallel with an axis of the magnetic body; and
      a target, the target being used to produce the radiation beam when the electrons collides onto the target, wherein a distance between the target and the axis of the magnetic body is greater than a distance between an accelerating tube of the linear accelerator and the axis of the magnetic body.

2. The radiation therapy system of claim 1, wherein the MRI apparatus further includes:
   one or more gradient coils arranged in the bore, the one or more gradient coils being around the axis of the magnetic body.

3. The radiation therapy system of claim 2, wherein the one or more gradient coils are split gradient coils.

4. The radiation therapy system of claim 3, wherein the linear accelerator is arranged within an opening formed by inner surfaces of the one or more gradient coils.

5. The radiation therapy system of claim 4, wherein the linear accelerator is disposed at or close to an end of the bore.

6. The radiation therapy system of claim 4, wherein the radiation therapy apparatus further includes an annular radiation shielding component surrounding the linear accelerator.

7. The radiation therapy system of claim 3, wherein the linear accelerator is located in a gap between two neighboring split gradient coils.

8. The radiation therapy system of claim 7, wherein the linear accelerator is arranged at or close to a mid-point of the bore in a length direction of the bore.

9. The radiation therapy system of claim 7, wherein the radiation therapy apparatus further includes a radiation shielding component surrounding a portion of the linear accelerator, the surrounded portion of the linear accelerator being closer to the axis of the magnetic body.

10. The radiation therapy system of claim 7, wherein the radiation therapy apparatus further includes:
at least one deflection magnet configured to deflect the electrons towards the target.

11. The radiation therapy system of claim 10, wherein the at least one deflection magnet includes a permanent magnet.

12. The radiation therapy system of claim 1, wherein the linear accelerator is located away from a path of the radiation beam from the target to the at least one portion of the ROI.

13. The radiation therapy system of claim 1, wherein the linear accelerator is located at a first position corresponding to a first circumferential angle of the bore, the target is located at a second position corresponding to a second circumferential angle of the bore, the first circumferential angle is unequal to the second circumferential angle, the first circumferential angle corresponds to a first radial direction in a cross section of the bore, the second circumferential angle corresponds to a second radial direction in the cross section of the bore, the first radial direction is different from the second radial direction, and the cross section of the bore is vertical to the axis of the magnetic body.

14. The radiation therapy system of claim 1, wherein the radiation therapy apparatus includes a microwave device configured to accelerate the electrons, the microwave device being operably coupled to the linear accelerator through a waveguide.

15. The radiation therapy system of claim 1, wherein the magnetic body includes:
a plurality of main magnetic coils;
a plurality of shielding coils, the plurality of shielding magnetic coils being around the axis of the magnetic body, and located along a circumference, or a portion thereof, with a larger radius from the axis of the magnetic body than the plurality of main magnetic coils; and
an annular cryostat in which the plurality of main magnetic coils and the plurality of shielding coils are arranged.

16. The radiation therapy system of claim 1, wherein the linear accelerator is located at a first position corresponding to a first circumferential angle of the bore, the target is located at a second position corresponding to a second circumferential angle of the bore, a difference between the first circumferential angle and the second circumferential angle is less than 90°, the first circumferential angle corresponds to a first radial direction in a cross section of the bore, the second circumferential angle corresponds to a second radial direction in the cross section of the bore, and the cross section of the bore is vertical to the axis of the magnetic body.

17. A method for applying a therapeutic radiation implemented on a computing device having at least one processor and at least one storage device, the method comprising:
acquiring magnetic resonance data with respect to a region of interest collected by a magnetic resonance imaging apparatus;
reconstructing an MR image of the ROI based on the MR data;
determining a parameter associated with the at least one portion of the ROI based on the MR image;
generating a control signal according to the parameter associated with the at least one portion of the ROI; and
sending the control signal to a radiation therapy apparatus to cause the radiation therapy apparatus to deliver a radiation beam to the at least one portion of the ROI, wherein the radiation therapy apparatus includes:
a linear accelerator configured to accelerate electrons to produce the radiation beam, the linear accelerator being located in a bore formed by an inner surface of the magnetic body, and a length direction of the linear accelerator being parallel with an axis of the magnetic body; and
a target, the target being used to produce the radiation beam when the electrons collides onto the target, wherein a distance between the target and the axis of the magnetic body is greater than a distance between an accelerating tube of the linear accelerator and the axis of the magnetic body.

18. The method of claim 17, wherein the MRI apparatus further includes one or more gradient coils arranged in the bore, the one or more gradient coils being around the axis of the magnetic body.

19. The method of claim 18, wherein the one or more gradient coils are split gradient coils.

20. The method of claim 19, wherein the linear accelerator is arranged within an opening formed by inner surfaces of the one or more gradient coils.

* * * * *